US011633084B2

United States Patent
Hirasawa et al.

(10) Patent No.: US 11,633,084 B2
(45) Date of Patent: Apr. 25, 2023

(54) IMAGE DIAGNOSIS ASSISTANCE APPARATUS, DATA COLLECTION METHOD, IMAGE DIAGNOSIS ASSISTANCE METHOD, AND IMAGE DIAGNOSIS ASSISTANCE PROGRAM

(71) Applicants: JAPANESE FOUNDATION FOR CANCER RESEARCH, Tokyo (JP); AI Medical Service Inc., Tokyo (JP)

(72) Inventors: Toshiaki Hirasawa, Tokyo (JP); Tomohiro Tada, Tokyo (JP); Kazuharu Aoyama, Tokyo (JP); Tsuyoshi Ozawa, Tokyo (JP); Toshiyuki Yoshio, Tokyo (JP)

(73) Assignees: JAPANESE FOUNDATION FOR CANCER RESEARCH, Tokyo (JP); AI MEDICAL SERVICE INC., Tokyo (JP)

( * ) Notice: Subject to any disclaimer, the term of this patent is extended or adjusted under 35 U.S.C. 154(b) by 175 days.

(21) Appl. No.: 16/760,458

(22) PCT Filed: Oct. 30, 2018

(86) PCT No.: PCT/JP2018/040381
§ 371 (c)(1),
(2) Date: Apr. 30, 2020

(87) PCT Pub. No.: WO2019/088121
PCT Pub. Date: May 9, 2019

(65) Prior Publication Data
US 2020/0337537 A1    Oct. 29, 2020

(30) Foreign Application Priority Data

Oct. 30, 2017 (JP) .............................. JP2017-209232
Jan. 22, 2018 (JP) .............................. JP2018-007967
Mar. 5, 2018 (JP) .............................. JP2018-038828

(51) Int. Cl.
*A61B 1/045* (2006.01)
*A61B 1/273* (2006.01)
(Continued)

(52) U.S. Cl.
CPC .. *A61B 1/000094* (2022.02); *A61B 1/000096* (2022.02); *A61B 1/045* (2013.01);
(Continued)

(58) Field of Classification Search
CPC .... G06V 20/80; G06V 20/695; G06V 30/147; G06V 30/1801; G06K 9/00523;
(Continued)

(56) References Cited

U.S. PATENT DOCUMENTS 9,589,374 B1* 3/2017 Gao ...................... A61B 6/5211
2008/0058593 A1* 3/2008 Gu ............................ G06T 5/40
600/109
(Continued)

FOREIGN PATENT DOCUMENTS

CN    102385664 A    3/2012
CN    106097335 A    11/2016
(Continued)

OTHER PUBLICATIONS

Harangi B, Hajdu A, Lampe R, Torok P. Recognizing ureter and uterine artery in endoscopic images using a convolutional neural network. In2017 IEEE 30th International Symposium on Computer-Based Medical Systems (CBMS) Jun. 22, 2012 (pp. 726-727). IEEE. (Year: 2017).*
(Continued)

*Primary Examiner* — Bobbak Safaipour
*Assistant Examiner* — Duy Tran
(74) *Attorney, Agent, or Firm* — Brundidge & Stanger, P.C.

(57) ABSTRACT

Provided are: an image diagnosis assistance apparatus capable of assisting diagnosis of an endoscopic image captured by an endoscopist; a data collection method; an image diagnosis assistance method; and an image diagnosis assistance program. The image diagnosis assistance apparatus is provided with: a lesion assessment unit that assesses, by a convolutional neural network, the denomination and the position of a lesion which is present in a digestive system endoscopic image of a patient captured by a digestive system endoscopic imaging device and information about accuracies thereof; and a display control unit that performs control for generating an analysis result image in which the denomination and the position of the lesion and the accuracies thereof are displayed and for displaying the image on the digestive system endoscopic image.

14 Claims, 32 Drawing Sheets

(51) Int. Cl.
| | | |
|---|---|---|
| *A61B 1/31* | (2006.01) | |
| *G06K 9/00* | (2022.01) | |
| *A61B 1/00* | (2006.01) | |
| *G06V 20/80* | (2022.01) | |
| *G06T 7/00* | (2017.01) | |

(52) U.S. Cl.
CPC ............... *A61B 1/273* (2013.01); *A61B 1/31* (2013.01); *G06T 7/0012* (2013.01); *G06V 20/80* (2022.01); *G06T 2207/10068* (2013.01); *G06T 2207/20084* (2013.01); *G06T 2207/30028* (2013.01)

(58) Field of Classification Search
CPC ....... G06T 7/0012; G06T 7/10; G06T 7/0014; G06T 9/002; G06T 2207/10068; G06T 2207/20084; G06T 2207/30028; G06T 2207/30056; G06T 2207/30004; G06T 2207/30084; G06T 2207/30096; G06T 2207/20112; A61B 1/044; A61B 1/045; A61B 1/273; A61B 1/307; A61B 1/31; A61B 1/0655
See application file for complete search history.

(56) References Cited

U.S. PATENT DOCUMENTS

| | | | | |
|---|---|---|---|---|
| 2011/0301447 A1* | 12/2011 | Park | ................ | A61B 1/000096 600/407 |
| 2012/0054652 A1 | 3/2012 | Kawagishi | | |
| 2013/0121548 A1* | 5/2013 | Kovalan | ................ | G06T 7/143 382/128 |
| 2014/0085686 A1 | 3/2014 | Ishihara | | |
| 2015/0213599 A1* | 7/2015 | Buzaglo | ............... | G06V 20/695 382/128 |
| 2016/0117818 A1* | 4/2016 | Park | ...................... | G06T 7/0012 382/131 |
| 2016/0321785 A1* | 11/2016 | Nishimura | ............ | G06T 3/4092 |
| 2018/0070798 A1 | 3/2018 | Kamiyama | | |
| 2019/0021580 A1 | 1/2019 | Mishima | | |
| 2019/0034800 A1 | 1/2019 | Shiratani | | |

FOREIGN PATENT DOCUMENTS

| | | |
|---|---|---|
| JP | 2002-165757 A | 6/2002 |
| JP | 2007-280229 A | 10/2007 |
| JP | 2017-045341 A | 3/2017 |
| JP | 2017-067489 A | 4/2017 |
| WO | 2012/165505 A1 | 12/2012 |
| WO | 2016/185617 A1 | 11/2016 |
| WO | 2017/170233 A1 | 10/2017 |
| WO | 2017/175282 A1 | 10/2017 |

OTHER PUBLICATIONS

Billah M, Waheed S, Rahman MM. An automatic gastrointestinal polyp detection system in video endoscopy using fusion of color wavelet and convolutional neural network features. International journal of biomedical imaging. Aug. 14, 2017;2017. (Year: 2017).*
R. Zhu, R. Zhang and D. Xue, "Lesion detection of endoscopy images based on convolutional neural network features," 2015 8th International Congress on Image and Signal Processing (CISP), 2015, pp. 372-376, doi: 10.1109/CISP.2015.7407907 (Year: 2015).*
Harangi B, Hajdu A, Lampe R, Torok P. Recognizing ureter and uterine artery in endoscopic images using a convolutional neural network. In2017 IEEE 30th International Symposium on Computer-Based Medical Systems (CBMS) Jun. 22, 2017 (pp. 726-727). IEEE (Year: 2017).*
Zou Y, Li L, Wang Y, Yu J, Li Y, Deng WJ. Classifying digestive organs in wireless capsule endoscopy images based on deep convolutional neural network. In2015 IEEE International Conference on Digital Signal Processing (DSP) Jul. 21, 2015 (pp. 1274-1278). IEEE. (Year: 2015).*
Zou Y, Li L, Wang Y, Yu J, Li Y, Deng WJ. Classifying digestive organs in wireless capsule endoscopy images based on deep convolutional neural network. In2015 IEEE International Conference on Digital Signal Processing (DSP) Jul. 21, 2015 (pp. 1274-1278). IEEE. (Year: 2015) (Year: 2015).*
Satoki Shichijo et al: "Application of Convolutional Neural Networks in the Diagnosis of Helicobacter pylori Infection Based onEndoscopic Images", EBIOMEDICINE, vol. 25, Oct. 14, 2017 (Oct. 14, 2017), pp. 106-111.
Extended European Search Report dated Aug. 6, 2021.
International Search Report from International Application No. PCT/JP2018/040381, dated Feb. 5, 2019.

* cited by examiner

FIG. 5

| MALE/FEMALE | 52/17 |
|---|---|
| AGE (MEDIAN) | 67 |
| TUMOR SIZE (MEDIAN) mm, RANGE | 24, 3-170 |
| LOCATION OF TUMOR | |
|    UPPER PART OF STOMACH | 14 |
|    MIDDLE PART OF STOMACH | 27 |
|    LOWER PART OF STOMACH | 33 |
|    ENTIRE REGION OF STOMACH | 3 |
| MACROSCOPIC CLASSIFICATION | |
|    TYPE 0-I | 1 |
|    TYPE 0-IIa | 8 |
|    TYPE 0-IIb | 3 |
|    TYPE 0-IIc | 38 |
|    COMBINED TYPE OF TYPE 0 (0-Ia+IIc, IIc+IIb, IIc+III) | 6 |
|    TYPE 1 | 1 |
|    TYPE 2 | 8 |
|    TYPE 3 | 6 |
|    TYPE 4 | 6 |
| TUMOR DEPTH | |
|    T1a (MUCOSA) | 43 |
|    T1b (SUBMUCOSA) | 9 |
|    T2 (MUSCULARIS PROPRIA) | 7 |
|    T3 (SUBSEROSA) | 2 |
|    T4a (SEROSA) | 16 |
| HISTOLOGICAL CLASSIFICATION | |
|    DIFFERENTIATED | 50 |
|    UNDIFFERENTIATED | 27 |

FIG. 9

| TUMOR DEPTH | TUMOR SIZE (mm) | | | |
|---|---|---|---|---|
| | ≤ 5 | 6-10 | 11-20 | ≥ 21 |
| T1a (MUCOSA) | 1/6(16.7) | 11/11(100) | 16/17(94.1) | 9/9(100) |
| T1b (SUBMUCOSA) | 0/0 | 0/0 | 1/1(100) | 8/8(100) |
| T2 (MUSCULARIS PROPRIA) | 0/0 | 0/0 | 0/0 | 7/7(100) |
| T3 (SUBSEROSA) | 0/0 | 0/0 | 0/0 | 2/2(100) |
| T4a (SEROSA) | 0/0 | 0/0 | 0/0 | 16/16(100) |

FIG. 10

| PATIENT | TUMOR SIZE (mm) | TUMOR DEPTH | MACROSCOPIC CLASSIFICATION | HISTOLOGICAL CLASSIFICATION |
|---|---|---|---|---|
| a | 3 | T1a | 0-IIc | DIFFERENTIATED |
| b | 4 | T1a | 0-IIc | DIFFERENTIATED |
| c | 4 | T1a | 0-IIc | DIFFERENTIATED |
| d | 5 | T1a | 0-IIc | DIFFERENTIATED |
| e | 5 | T1a | 0-IIc | DIFFERENTIATED |
| f | 16 | T1a | 0-IIc | DIFFERENTIATED |

FIG. 12

| GASTRITIS (REDNESS, ATROPHY, INTESTINAL METAPLASIA) | 76 |
|---|---|
| NORMAL ANATOMICAL STRUCTURE (CARDIA, PYLORUS, ANGULAR INCISURE) | 28 |
| FOLD | 8 |
| BLOOD | 8 |
| MUCUS | 8 |
| SCAR | 7 |
| HALATION | 6 |
| PERISTALSIS | 4 |
| VASA | 3 |
| XANTHOMA | 3 |
| SUCTION MARK | 2 |
| BUBBLE | 2 |
| HYPERPLASTIC POLYP | 2 |
| FOCAL BLUR | 2 |
| SUBMUCOSAL TUMOR | 1 |
| EXTRAMURAL PRESSURE | 1 |

| LEARNING DATA SET | | | | |
|---|---|---|---|---|
| COLORECTAL POLYP TYPE | NUMBER OF POLYPS (%) | WHITE LIGHT (IMAGE) | NBI NARROW-BAND LIGHT (IMAGE) | TOTAL NUMBER OF IMAGES |
| ADENOMA | 3,513(74) | 9,310(53) | 2,085(73) | 11,395(56) |
| HYPERPLASTIC POLYP | 1,058(22) | 2,002(11) | 519(18) | 2,521(12) |
| SSAP | 22(0) | 116(1) | 23(1) | 139(1) |
| ADENOCARCINOMA | 68(1) | 1,468(8) | 131(5) | 1,599(8) |
| OTHERS | 91(2) | 657(4) | 107(4) | 764(4) |
| NORMAL | - | 4,013(23) | 0(0) | 4,013(20) |
| TOTAL | 4,752(100) | 17,566(100) | 2,865(100) | 20,431(100) |

FIG. 17

| ASSESSMENT TEST DATA SET | | | | | |
|---|---|---|---|---|---|
| COLORECTAL POLYP TYPE | SIZE | NUMBER OF POLYPS (%) | WHITE LIGHT (IMAGE) | NBI NARROW-BAND LIGHT (IMAGE) | TOTAL NUMBER OF IMAGES |
| ADENOMA N=218 PROTRUDING: 199 FLAT: 19 | ≤ 5 mm | 156(50) | 638(10) | 208(63) | 846(12) |
| | 5-9 mm | 52(17) | | | |
| | ≥ 10 mm | 10(3) | | | |
| HYPERPLASTIC POLYP N=63 PROTRUDING: 53 FLAT: 10 | ≤ 5 mm | 56(18) | 137(2) | 71(21) | 208(3) |
| | 5-9 mm | 7(2) | | | |
| | ≥ 10 mm | 0(0) | | | |
| SSAP N=7 PROTRUDING: 1 FLAT: 6 | ≤ 5 mm | 0(0) | 40(1) | 8(2) | 48(1) |
| | 5-9 mm | 4(1) | | | |
| | ≥ 10 mm | 3(1) | | | |
| ADENOCARCINOMA (SIZE ≥ 10 mm) N=4 | | 4(1) | 30(0) | 3(1) | 33(0) |
| OTHERS (SIZE ≤ 5 mm) N=17 | | 17(6) | 27(0) | 10(3) | 37(1) |
| NORMAL | | - | 5,874(87) | 31(9) | 5,905(83) |
| TOTAL | | 309(100) | 6,750(100) | 331(100) | 7,081(100) |

FIG. 18

| FALSE-POSITIVE IMAGE (N=165) | | |
|---|---|---|
| CATEGORY | SUB-CATEGORY | NUMBER (%) |
| NORMAL STRUCTURE | ILEOCECAL VALVE | 56(34) |
| | APPENDICEAL ORIFICE | 6(4) |
| | ANUS | 2(1) |
| COLONIC FOLDS | | 55(33) |
| FECES | | 4(2) |
| TRUE POLYP? | | 12(7) |
| OTHERS | HALATION | 14(8) |
| | NORMAL MUCOSA | 8(5) |
| | FOGGING OF CAMERA LENS SURFACE | 4(2) |
| | BLUR | 2(1) |
| | SCAR AFTER POLYP RESECTION | 1(1) |
| | VASODILATION | 1(1) |
| FALSE-NEGATIVE IMAGE (N=89) | | |
| TEXTURE OF SURFACE OF COLORECTAL POLYP WAS LESS RECOGNIZABLE BECAUSE OF SMALL OR DARK COLORECTAL POLYP | | 50(56) |
| COLORECTAL POLYP WAS CAPTURED FROM EITHER SIDE OR PORTION THEREOF WAS CAPTURED | | 34(38) |
| COLORECTAL POLYP WAS VERY LARGE | | 5(6) |

FIG. 19A

| | WHITE LIGHT | | | | | |
|---|---|---|---|---|---|---|
| | | CNN CLASSIFICATION (%) | | | | |
| | | ADENOMA | HYPERPLASTIC POLYP | SSAP | ADENOCARCINOMA | OTHERS |
| HISTOLOGICAL CLASSIFICATION | ADENOMA | 562(97) | 14(2) | 0(0) | 4(1) | 2(0) |
| | HYPERPLASTIC POLYP | 64(51) | 59(47) | 0(0) | 0(0) | 2(2) |
| | SSAP | 6(26) | 12(52) | 5(22) | 0(0) | 0(0) |
| | ADENOCARCINOMA | 6(21) | 0(0) | 0(0) | 23(79) | 0(0) |
| | OTHERS | 14(58) | 7(29) | 0(0) | 0(0) | 3(13) |

FIG. 19B

| | NBI NARROW-BAND LIGHT | | | | | |
|---|---|---|---|---|---|---|
| | | CNN CLASSIFICATION (%) | | | | |
| | | ADENOMA | HYPERPLASTIC POLYP | SSAP | ADENOCARCINOMA | OTHERS |
| HISTOLOGICAL CLASSIFICATION | ADENOMA | 197(97) | 5(2) | 0(0) | 1(0) | 0(0) |
| | HYPERPLASTIC POLYP | 31(46) | 37(54) | 0(0) | 0(0) | 0(0) |
| | SSAP | 2(33) | 4(67) | 0(0) | 0(0) | 0(0) |
| | ADENOCARCINOMA | 3(100) | 0(0) | 0(0) | 0(0) | 0(0) |
| | OTHERS | 3(30) | 7(70) | 0(0) | 0(0) | 0(0) |

FIG. 20

| | WHITE LIGHT | | |
|---|---|---|---|
| | | CNN CLASSIFICATION (%) | | |
| | | ADENOMA | HYPERPLASTIC POLYP | OTHERS |
| HISTOLOGICAL CLASSIFICATION | ADENOMA | 348(98) | 8(2) | 0 |
| | HYPERPLASTIC POLYP | 49(49) | 50(50) | 1(1) |
| | OTHERS | 14(58) | 7(29) | 3(13) |

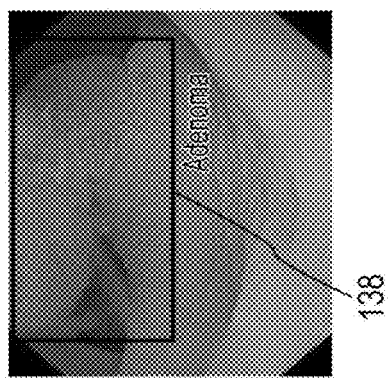
FIG. 22D
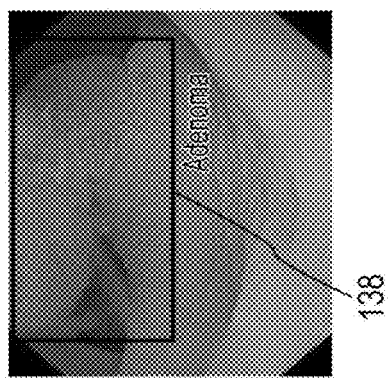
FIG. 22C
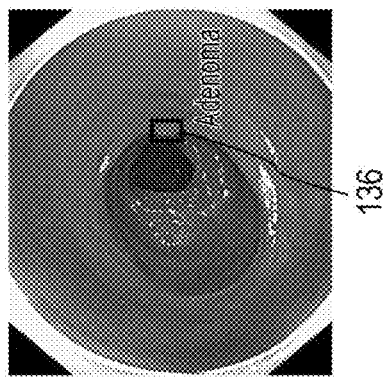
FIG. 22B
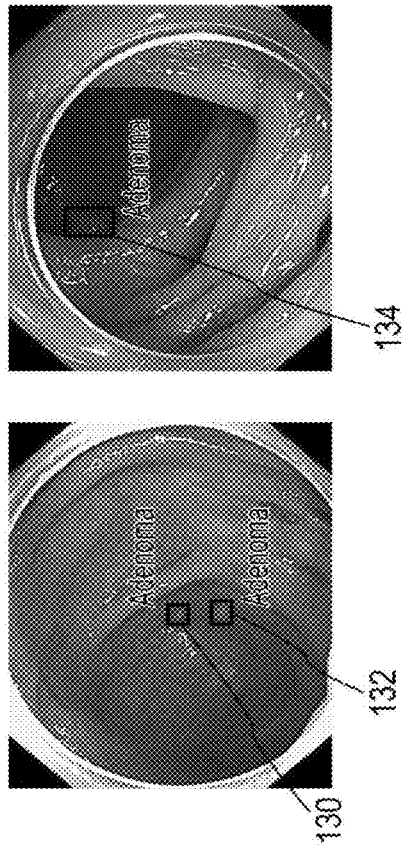
FIG. 22A
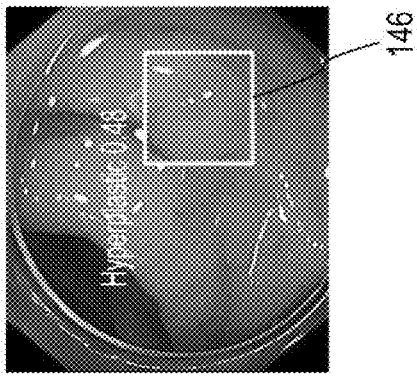
FIG. 22H
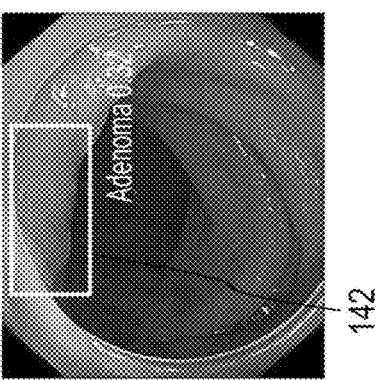
FIG. 22G
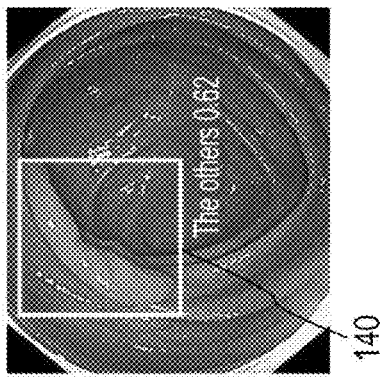
FIG. 22F
FIG. 22E

FIG. 23

| FEATURES OF PATIENT (n = 47) | |
|---|---|
| MALE/FEMALE | 41/6 |
| AGE: MEDIAN/RANGE | 70/48-81 |
| FEATURES OF LESION (n = 49) | |
| TUMOR SIZE (MEDIAN) mm, RANGE | 20/5-700 |
| LOCATION OF TUMOR: Ce/Ut/Mt/Lt/Ae | 0/8/23/10/8 |
| MACROSCOPIC CLASSIFICATION | |
| SUPERFICIAL: TYPE 0-IIa, TYPE 0-IIb, TYPE 0-IIc | 1/6/13/23 |
| ADVANCED: 1/2/3/4 | 0/3/3/0 |
| TUMOR DEPTH: T1a/T1b/T2-4 | 40/2/7 |
| HISTOPATHOLOGY: SQUAMOUS CELL CARCINOMA (ESCC)/ADENOCARCINOMA (EAC) | 41/8 |

FIG. 25

|  |  | BIOPTIC RESULTS | |
|---|---|---|---|
|  |  | ESOPHAGEAL CANCER | NON-ESOPHAGEAL CANCER |
| CNN DETECTION RESULTS WITH WHITE LIGHT | ESOPHAGEAL CANCER | 38 | 35 |
|  | NON-ESOPHAGEAL CANCER | 9 | 15 |
| CNN DETECTION RESULTS WITH NBI NARROW-BAND LIGHT | ESOPHAGEAL CANCER | 41 | 28 |
|  | NON-ESOPHAGEAL CANCER | 5 | 22 |
| COMPREHENSIVE CNN DETECTION RESULTS | ESOPHAGEAL CANCER | 46 | 42 |
|  | NON-ESOPHAGEAL CANCER | 1 | 8 |

FIG. 27

|  |  | BIOPTIC RESULTS ||
|  |  | ESOPHAGEAL CANCER | NON-ESOPHAGEAL CANCER |
| --- | --- | --- | --- |
| CNN DETECTION RESULTS WITH WHITE LIGHT | ESOPHAGEAL CANCER | 61 | 105 |
|  | NON-ESOPHAGEAL CANCER | 28 | 364 |
| CNN DETECTION RESULTS WITH NBI NARROW-BAND LIGHT | ESOPHAGEAL CANCER | 64 | 85 |
|  | NON-ESOPHAGEAL CANCER | 15 | 396 |

FIG. 29

|  | WHITE LIGHT | NBI NARROW-BAND LIGHT | ALL ENDOSCOPIC IMAGES |
|---|---|---|---|
| SUPERFICIAL ESOPHAGEAL CANCER | 100%(75/75) | 99%(67/68) | 99%(142/143) |
| ADVANCED ESOPHAGEAL CANCER | 100%(14/14) | 82%(9/11) | 92%(23/25) |
| ALL ESOPHAGEAL CANCERS | 100%(89/89) | 96%(76/79) | 98%(165/168) |

FIG. 30

| FALSE-POSITIVE IMAGE | NUMBER (%) |
|---|---|
| CONTAINED SHADOW | 95(50) |
| NORMAL STRUCTURE LIKELY TO BE IDENTIFIED AS ESOPHAGEAL CANCER (ESOPHAGEAL GASTRIC JUNCTION/LEFT MAIN BRONCHUS/VERTEBRAL BODY) | 61(32) (29/25/7) |
| BENIGN LESION LIKELY TO BE MIS-DIAGNOSED AS ESOPHAGEAL CANCER (POSTOPERATIVE SCAR/FOCAL ATROPHY/BARRETT'S ESOPHAGUS/ INFLAMMATION/INTRAEPITHELIAL NEOPLASIA/KERATINIZATION/ECTOPIC GASTRIC MUCOSA) | 32(17) (13/9/5/4/1/1/1) |

| FALSE-NEGATIVE IMAGE | NUMBER (%) |
|---|---|
| MIS-DIAGNOSED AS INFLAMMATION OF BACKGROUND MUCOSA | 10(25) |
| BLURRED IMAGE OF SQUAMOUS CELL CARCINOMA (ESCC) WITH NBI NARROW-BAND LIGHT | 7(17) |
| INSUFFICIENT LEARNING ABOUT ADENOCARCINOMA (EAC) | 4(10) |
| DIFFICULT TO DIAGNOSE (LESION APPEARING IN BACKGROUND, PRESENCE OF ONLY PORTION OF LESION) | 20(49) |

IMAGE DIAGNOSIS ASSISTANCE APPARATUS, DATA COLLECTION METHOD, IMAGE DIAGNOSIS ASSISTANCE METHOD, AND IMAGE DIAGNOSIS ASSISTANCE PROGRAM

TECHNICAL FIELD

The present invention relates to a diagnostic imaging support apparatus, a data collection method, a diagnostic imaging support method, and a diagnostic imaging support program.

BACKGROUND ART

Cancer is a disease that is the most likely cause of death in the world. According to the World Health Organization (WHO) statistics, 8.8 million people died of cancers in 2015, and, when classified by organ system, the cancers in the digestive system, including gastric cancer, colonic cancer, and so forth, are leading causes of death. In particular, gastric cancer is the fifth most common malignant tumor in the world and the third common cause of cancer-related death in the world. About 1 million new cases occur every year, and about 700,000 people die. The prognosis of gastric cancer patients depends on the stage (progression) of the cancer at the time of diagnosis. Although advanced gastric cancer has a poor prognosis, the five-year survival rate of early gastric cancer is 90% or more, and many gastric cancers are completely curable if early lesions are detected and surgically resected at an early stage. Accordingly, endoscopic detection of early gastric cancer is the most effective procedure to reduce gastric cancer mortality, and the spread of the technique of treating with organ-preserving endoscopic therapy such as endoscopic mucosal resection (EMR) or endoscopic submucosal dissection (ESD) can bring great benefits to patients.

Endoscopy of the digestive organs (in particular, upper gastrointestinal tract endoscopy: EGD) is a standard method for diagnosing gastric cancer, but is said to generate a false-negative rate of 26% when detecting gastric cancer by observation using EGD (see NPL 1), and gastric cancers are missed with high frequency. In addition, most gastric cancers arise from atrophic mucosa, and some early gastric cancers show only subtle morphological changes and are difficult to distinguish from background mucosa with atrophic changes. Less experienced endoscopists tend to miss gastric cancer. Therefore, special training and experience are required for the endoscopist to properly detect gastric cancer. However, it is said that experience of diagnosis with 10,000 images and 10 years of experience are taken to train an endoscopist who has a certain level of experience.

In endoscopy of the digestive organs, many endoscopic images are collected. It is desirable for the endoscopist to double-check the endoscopic images to manage diagnostic accuracy, and double-checking is mandatory in "Taisakugata kenshin no tameno i naishikyo kenshin manyuaru (Gastroscopy screening guidelines for population based screening)" (ed. Japanese Society of Gastrointestinal Cancer Screening). However, double-checking endoscopic images requires a large amount of time and imposes a heavy load on endoscopists in medical situations.

In addition, diagnosis based on such endoscopic images is a so-called subjective determination based on experience and observation and may cause various false-positive decisions and false-negative decisions. Furthermore, the best performance of a medical device is achieved only when both conditions of the performance of the device itself and the reliable operation of the operator are satisfied. However, endoscopic diagnosis may reduce accuracy due to the fatigue of the endoscopist. To compensate for such personal requirements of endoscopists, AI (artificial intelligence), which has dramatically improved the accuracy of image recognition by machine learning in recent years, is used to support endoscopists. Therefore, it is expected that the accuracy and speed of the double-check operation of endoscopic images will be improved.

In recent years, AI using deep learning has attracted attention in various medical fields, and there are various reports that AI can perform diagnostic imaging in medical fields, including radiation oncology, skin cancer classification, diabetic retinopathy, histological classification of gastric biopsy, and characterization of colonic lesions with ultra-magnifying endoscopy, on behalf of specialists. In particular, it has been proven that, at the microscopic/endoscopic level, AI can provide accuracy equivalent to that of a specialist (see NPL 2). Further, in dermatology, it has been announced that an AI having a deep learning function exhibits diagnostic imaging capability equivalent to that of a specialist (see NPL 3), and there are also PTLs (see PTLs 1 and 2) in which various machine learning methods are utilized.

CITATION LIST

Patent Literature

PTL 1
Japanese Patent Application Laid-Open No. 2017-045341
PTL 2
Japanese Patent Application Laid-Open No. 2017-067489

Non-Patent Literature

NPL 1
Hosokawa O et al., Hepatogastroenterology. 2007; 54(74): 442-4.
NPL 2
http://www.giejournal.org/article/S0016-5107(14)02171-3/fulltext, "Novel computer-aided diagnostic system for colorectal lesions by using endocytoscopy" Yuichi Mori et. al. Presented at Digestive Disease Week 2014, May 3-6, 2014, Chicago, Ill., USA
NPL 3
"Dermatologist-level Classification of Skin Cancer with Deep Neural Networks", the opening article of the February 2017 issue of "Nature" (http://www.natureasia.com/ja-jp/nature/highlights/82762)

SUMMARY OF INVENTION

Technical Problem

As described above, it is suggested that the image recognition capability of AI is comparable to that of a human specialist. In normal endoscopy of the digestive organs, however, the diagnostic support technology using AI's ability of diagnosis with endoscopic images has not yet been introduced in medical situations and is now expected to be put into practical use in the future.

It is an object of the present invention to provide a diagnostic imaging support apparatus, a data collection method, a diagnostic imaging support method, and a diagnostic imaging support program that are capable of supporting an endoscopist in diagnosis with endoscopic images.

SOLUTION TO PROBLEM

A diagnostic imaging support apparatus according to the present invention include:

a lesion estimation section that estimates a name and a location of a lesion present in a digestive-organ endoscopic image of a subject and information on certainty of the name and the location of the lesion using a convolutional neural network, the digestive-organ endoscopic image being captured by a digestive-organ endoscopic image capturing apparatus; and a display control section that performs control to generate an analysis result image showing the name and the location of the lesion and the certainty of the name and the location of the lesion and to display the analysis result image on the digestive-organ endoscopic image, in which the convolutional neural network is subjected to a learning process based on lesion names and lesion locations of lesions present in a plurality of digestive-organ tumor endoscopic images, the lesion names and the lesion locations of the lesions being determined in advance through feature extraction of atrophy, intestinal metaplasia, mucosal swelling or depression, and a condition of mucosal color tones.

A data collection method according to the present invention is a method for collecting, using the diagnostic imaging support apparatus described above, a display result of the display control section as data related to a gastrointestinal tract lesion for a gastrointestinal tract of a subject.

A diagnostic imaging support method according to the present invention is a method using an apparatus, the apparatus including:

a lesion estimation section that estimates a name and a location of a lesion present in a digestive-organ endoscopic image of a subject and information on certainty of the name and the location of the lesion using a convolutional neural network, the digestive-organ endoscopic image being captured by a digestive-organ endoscopic image capturing apparatus, and a display control section that performs control to generate an analysis result image showing the name and the location of the lesion and the certainty of the name and the location of the lesion and to display the analysis result image on the digestive-organ endoscopic image, and the diagnostic imaging support method comprising subjecting the convolutional neural network to a learning process based on lesion names and lesion locations of lesions present in a plurality of digestive-organ tumor endoscopic images, the lesion names and the lesion locations of the lesions being determined in advance through feature extraction of atrophy, intestinal metaplasia, mucosal swelling or depression, and a condition of mucosal color tones.

A diagnostic imaging support program according to the present invention is a program for causing a computer to execute:

a process of estimating a name and a location of a lesion present in a digestive-organ endoscopic image of a subject and information on certainty of the name and the location of the lesion using a convolutional neural network, the digestive-organ endoscopic image being captured by a digestive-organ endoscopic image capturing apparatus; and a process of performing control to generate an analysis result image showing the name and the location of the lesion and the certainty of the name and the location of the lesion and to display the analysis result image on the endoscopic image, in which the convolutional neural network is subjected to a learning process based on lesion names and lesion locations of lesions present in a plurality of digestive-organ tumor endoscopic images, the lesion names and the lesion locations of the lesions being determined in advance through feature extraction of atrophy, intestinal metaplasia, mucosal swelling or depression, and a condition of mucosal color tones.

The standard for determination using feature extraction of lesion sites (atrophy, intestinal metaplasia, mucosal swelling or depression, and a condition of mucosal color tones) according to the present invention can be set by an experienced endoscopist with high accuracy and is described in detail in, for example, a book written by one of the present inventors ("Detection and Diagnosis of Early Gastric Cancer—Using Conventional Endoscopy", Toshiaki Hirasawa/Hiroshi Kawachi (authors), Junko Fujisaki (supervising editor), Nihon Medical Center, 2016).

Advantageous Effects of Invention

According to the present invention, it is possible to provide a technique for supporting an endoscopist in diagnosis with endoscopic images.

BRIEF DESCRIPTION OF DRAWINGS

FIG. 5 is a diagram illustrating features of patients and lesions related to endoscopic images used for assessment test data sets;

FIG. 9 is a diagram illustrating a change in sensitivity depending on different tumor depths and tumor sizes;

FIG. 10 is a diagram illustrating the details of lesions missed by the convolutional neural network;

FIG. 12 is a diagram illustrating the details of noncancerous lesions detected as gastric cancer by the convolutional neural network;

FIG. 16 is a diagram illustrating features of colorectal polyps and the like related to endoscopic images used for learning data sets;

FIG. 17 is a diagram illustrating features of colorectal polyps and the like related to endoscopic images used for assessment test data sets;

FIG. 18 is a diagram illustrating classification results of false-positive images and false-negative images;

FIGS. 19A and 19B are diagrams illustrating degrees of match between CNN classification and histological classification;

FIG. 20 is a diagram illustrating degrees of match between CNN classification and histological classification for colorectal polyps of 5 mm or less;

FIGS. 22A, 22B, 22C, 22D, 22E, 22F, 22G, and 22H are diagrams illustrating an example of endoscopic images and analysis result images in the second assessment test;

FIG. 23 is a diagram illustrating features of patients and lesions related to endoscopic images used for assessment test data sets;

FIG. 25 is a diagram illustrating detection results of esophageal cancer/non-esophageal cancer by the convolutional neural network and detection results of esophageal cancer/non-esophageal cancer via biopsy;

FIG. 27 is a diagram illustrating detection results of esophageal cancer/non-esophageal cancer by the convolutional neural network and detection results of esophageal cancer/non-esophageal cancer via biopsy;

FIG. 29 is a diagram illustrating degrees of match between CNN classification and the depth of invasion;

FIG. 30 is a diagram illustrating classification results of false-positive images and false-negative images;

DESCRIPTION OF EMBODIMENTS

The following describes an embodiment of the present invention in detail with reference to the drawings.

[Overall Configuration of Diagnostic Imaging Support Apparatus]

Figure 1:
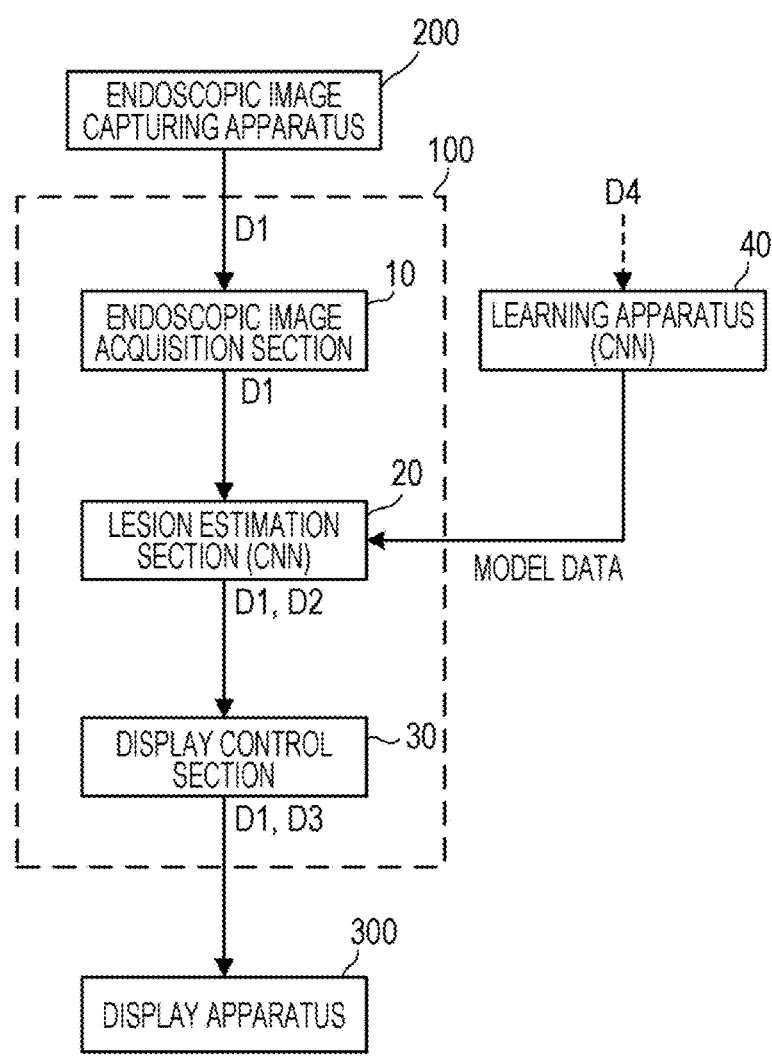
FIG. 1 is a block diagram illustrating an overall configuration of a diagnostic imaging support apparatus according to this embodiment.
Figure 2:
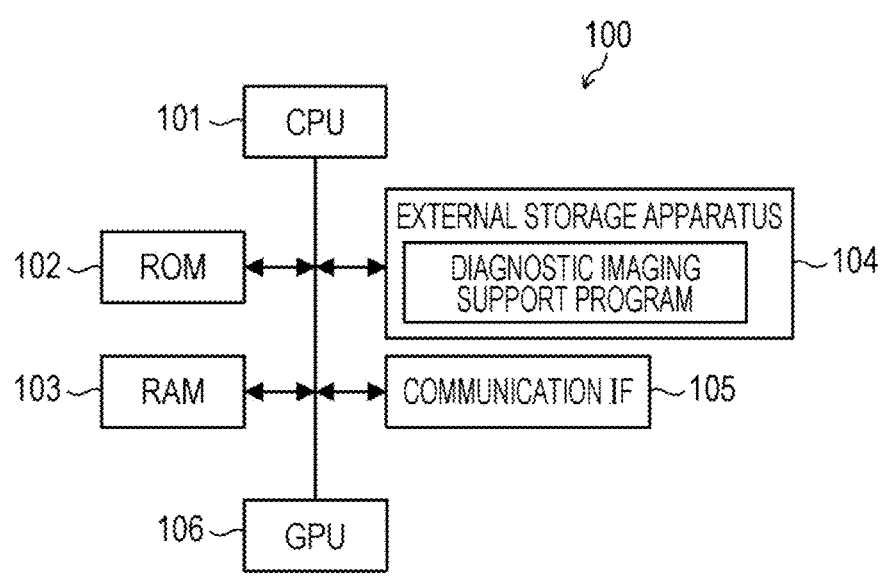
FIG. 2 is a diagram illustrating a hardware configuration of the diagnostic imaging support apparatus according to this embodiment.

First, a configuration of diagnostic imaging support apparatus 100 according to this embodiment will be described. FIG. 1 is a block diagram illustrating an overall configuration of diagnostic imaging support apparatus 100. FIG. 2 is a diagram illustrating an example hardware configuration of diagnostic imaging support apparatus 100 according to this embodiment.

Diagnostic imaging support apparatus 100 is used for endoscopy of the digestive organs (for example, the esophagus, stomach, duodenum, large intestine, etc.) and supports a doctor (for example, an endoscopist) in diagnosis based on endoscopic images by using the diagnostic endoscopic imaging capability of a convolutional neural network (CNN). Diagnostic imaging support apparatus 100 is connected to endoscopic image capturing apparatus 200 (corresponding to a "digestive-organ endoscopic image capturing apparatus" of the present invention) and display apparatus 300.

Examples of endoscopic image capturing apparatus 200 include an electronic endoscope containing a built-in imaging section (also called a videoscope), and a camera-equipped endoscope that is an optical endoscope with a camera head having a built-in imaging section. Endoscopic image capturing apparatus 200 is inserted from, for example, the mouth or nose of a subject into a digestive organ to capture an image of a diagnostic target site in the digestive organ. Then, endoscopic image capturing apparatus 200 outputs endoscopic image data D1 (still image) indicating a captured endoscopic image of the diagnostic target site in the digestive organ (corresponding to a "digestive-organ endoscopic image" of the present invention) to diagnostic imaging support apparatus 100. In place of endoscopic image data D1, an endoscopic moving image may be used.

Display apparatus 300, examples of which include a liquid crystal display, displays an analysis result image, which is output from diagnostic imaging support apparatus 100, to the doctor in an identifiable manner.

Diagnostic imaging support apparatus 100 is a computer including main components, such as CPU (Central Processing Unit) 101, ROM (Read Only Memory) 102, RAM (Random Access Memory) 103, external storage apparatus (for example, a flash memory) 104, communication interface 105, and GPU (Graphics Processing Unit) 106.

The functions of diagnostic imaging support apparatus 100 are implemented by, for example, CPU 101 referring to a control program (for example, a diagnostic imaging support program), various data (for example, endoscopic image data, teacher data, model data (such as structured data and learned weight parameters) of the convolutional neural network), and so on that are stored in ROM 102, RAM 103, external storage apparatus 104, or the like. RAM 103 functions as, for example, a work area or temporary storage area of data.

All or some of the functions may be implemented by processing performed by a DSP (Digital Signal Processor) in place of or in addition to processing performed by the CPU. Also, all or some of the functions may be implemented by processing performed by a dedicated hardware circuit in place of or in addition to processing performed by software.

As illustrated in FIG. 1, diagnostic imaging support apparatus 100 includes endoscopic image acquisition section 10, lesion estimation section 20, and display control section 30. Learning apparatus 40 has a function of generating model data (such as structured data and learned weight parameters) of the convolutional neural network, which is used in diagnostic imaging support apparatus 100.

[Image Acquisition Section]

Image acquisition section 10 acquires endoscopic image data D1 output from endoscopic image capturing apparatus 200. Then, image acquisition section 10 outputs acquired endoscopic image data D1 to lesion estimation section 20.

Image acquisition section 10 may acquire endoscopic image data D1 directly from endoscopic image capturing apparatus 200 or may acquire endoscopic image data D1 stored in external storage apparatus 104 or endoscopic image data D1 provided via an Internet line or the like.

[Lesion Estimation Section]

Lesion estimation section 20 estimates a lesion name (name) and lesion location (location) of a lesion present in an endoscopic image represented by endoscopic image data D1 output from the endoscopic image acquisition section 10, and also estimates the certainty of the lesion name and the lesion location by using the convolutional neural network. Then, lesion estimation section 20 outputs to display control section 30 endoscopic image data D1 output from the endoscopic image acquisition section 10 and estimation result data D2 indicating the estimation results of the lesion name, the lesion location, and the certainty.

In this embodiment, lesion estimation section 20 estimates a probability score as an index indicating the certainty of a lesion name and a lesion location. The probability score is represented by a value greater than 0 and less than or equal to 1. A higher probability score indicates a higher certainty of a lesion name and a lesion location.

The probability score is an example index indicating the certainty of a lesion name and a lesion location. Any other suitable index may instead be used. For example, the probability score may be represented by a value of 0% to 100% or may be represented by any one of several level values.

A convolutional neural network is a type of feedforward neural network and is based on findings in the structure of the visual cortex of the brain. The convolutional neural network basically has a structure in which a convolution layer responsible for local feature extraction from an image and a pooling layer (subsampling layer) for summarizing features for each local region are repeated. Each layer of the convolutional neural network has a plurality of neurons and is arranged such that each neuron corresponds to that of the visual cortex. The fundamental function of each neuron has signal input and output. Note that when transmitting signals to each other, neurons in each layer do not directly output signals that are input, but each input is assigned a coupling load such that when the sum of the weighted inputs exceeds a threshold that is set for each neuron, the neuron outputs signals to the neurons in the subsequent layer. The respective coupling loads between the neurons are calculated from learning data. This enables estimation of an output value in response to input of real-time data. Any convolutional neural network that achieves the object described above may be used, regardless of which algorithm it has.

Figure 3:
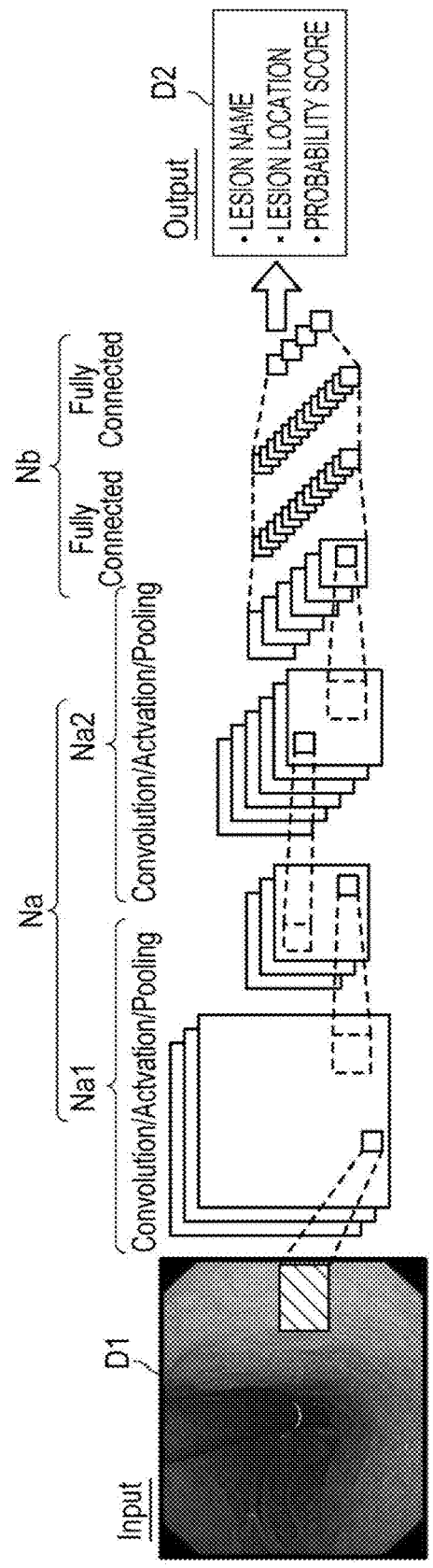
FIG. 3 is a diagram illustrating a configuration of a convolutional neural network according to this embodiment.

FIG. 3 is a diagram illustrating a configuration of a convolutional neural network according to this embodiment. The model data (such as structured data and learned weight parameters) of the convolutional neural network is stored in external storage apparatus 104 together with the diagnostic imaging support program.

As illustrated in FIG. 3, the convolutional neural network has, for example, feature extraction section Na and identification section Nb. Feature extraction section Na performs a process of extracting image features from an input image (endoscopic image data D1). Identification section Nb outputs image-related estimation results from the image features extracted by feature extraction section Na.

Feature extraction section Na is constituted by a plurality of feature value extraction layers Na1, Na2, . . . that are hierarchically connected to each other. Feature value extraction layers Na1, Na2, . . . each include a convolution layer, an activation layer, and a pooling layer.

Feature value extraction layer Na1 as the first layer performs a raster scan on an input image to scan each predetermined size. Then, feature value extraction layer Na1 performs a feature value extraction process on the scanned data using the convolution layer, the activation layer, and the pooling layer to extract feature values from the input image. Feature value extraction layer Na1 as the first layer extracts, for example, comparatively simple single feature values such as feature values of horizontally extending lines or feature values of diagonally extending lines.

Feature value extraction layer Na2 as the second layer performs, for example, a raster scan on an image (also referred to as a feature map) input from feature value extraction layer Na1 as the preceding layer to scan each predetermined size. Then, feature value extraction layer Na2 performs a feature value extraction process on the scanned data using the convolution layer, the activation layer, and the pooling layer in a similar way to extract feature values from the input image. Feature value extraction layer Na2 as the second integrates a plurality of feature values extracted by feature value extraction layer Na1 as the first layer by referring to a positional relationship and the like of the plurality of feature values to extract higher-order composite feature values.

The feature value extraction layers as the second and subsequent layers (in FIG. 3, only two feature value extraction layers Na are illustrated, for convenience of description) execute processing similar to that of feature value extraction layer Na2 as the second layer. Then, the output (respective map values in a plurality of feature maps) of the final feature value extraction layer is input to identification section Nb.

Identification section Nb is constituted by, for example, a multilayer perceptron in which a plurality of fully connected layers are hierarchically connected to each other.

The fully connected layer on the input side of identification section Nb is fully connected to the respective map values in the plurality of feature maps, which are acquired from feature extraction section Na, performs the multiply-and-accumulate operation on the respective values while applying changing weight coefficients, and outputs the result.

The fully connected layer in the subsequent hierarchical layer of identification section Nb is fully connected to values output from the elements in the fully connected layer in the preceding hierarchical layer, and performs the multiply-and-accumulate operation on the respective values while applying changing weight coefficients. Then, identification section Nb has in the final stage thereof a layer (for example, softmax function or the like) from which a lesion name and lesion location of a lesion present in the endoscopic image and the probability score (certainty) of the lesion name and the lesion location are output.

The convolutional neural network can have an estimation function such that the convolutional neural network is subjected to a learning process using reference data (hereinafter referred to as "teacher data") obtained in advance by an experienced endoscopist through marking processing so that desired estimation results (here, a lesion name, a lesion location, and a probability score) can be output from an input endoscopic image.

The convolutional neural network according to this embodiment is configured to receive input of endoscopic image data D1 ("input" in FIG. 3) and output a lesion name, a lesion location, and a probability score for an image feature of an endoscopic image represented by endoscopic image data D1 as estimation result data D2 ("output" in FIG. 3).

More preferably, the convolutional neural network may have a configuration capable of receiving input of, in addition to endoscopic image data D1, information related to the age, gender, geographic area, or past medical history (for example, this configuration is provided as an input element of identification section Nb). Since the importance of real-world data in the actual clinical situation is recognized in particular, addition of information on such patient attributes enables development of the convolutional neural network to a more useful system in the actual clinical situation. That is, the features of the endoscopic image have a correlation with information related to the age, gender, geographic area, or past medical history, and causing the convolutional neural network to refer to patient attribute information such as age, in addition to endoscopic image data D1, provides a configuration capable of estimating a lesion name and a lesion location with higher accuracy. This method is a matter to be incorporated particularly when the present invention is internationally used, since the state of a disease may differ depending on the geographic area or race.

In addition to the processing performed by the convolutional neural network, lesion estimation section 20 may perform pre-processing, examples of which include processing for conversion into the size or aspect ratio of the endoscopic image, color separation processing of the endoscopic image, color conversion processing of the endoscopic image, color extraction processing, and brightness gradient extraction processing.

[Display Control Section]

Display control section 30 generates an analysis result image showing a lesion name, a lesion location, and a probability score indicated by estimation result data D2, which is output from lesion estimation section 20, on an endoscopic image represented by endoscopic image data D1 output from lesion estimation section 20. Then, display control section 30 outputs endoscopic image data D1 and analysis result image data D3 representing the generated analysis result image to display apparatus 300. In this case, a digital image processing system for highlighting the structure of a lesion part of the endoscopic image, displaying the lesion part in a highlighted color, providing high contrast, providing high definition, or the like may be connected to perform processing to help the observer gain understanding and determination.

Display apparatus 300 displays an analysis result image represented by analysis result image data D3 on an endoscopic image represented by endoscopic image data D1 output from display control section 30. The displayed endoscopic image and analysis result image are used for the double-check operation of the endoscopic image, for example. In this embodiment, furthermore, it takes a very short time to display each endoscopic image and each analysis result image, and thus, in addition to the double-check operation of endoscopic images, the use of an endoscopic moving image can assist a doctor in real-time diagnosis.

Figure 4:
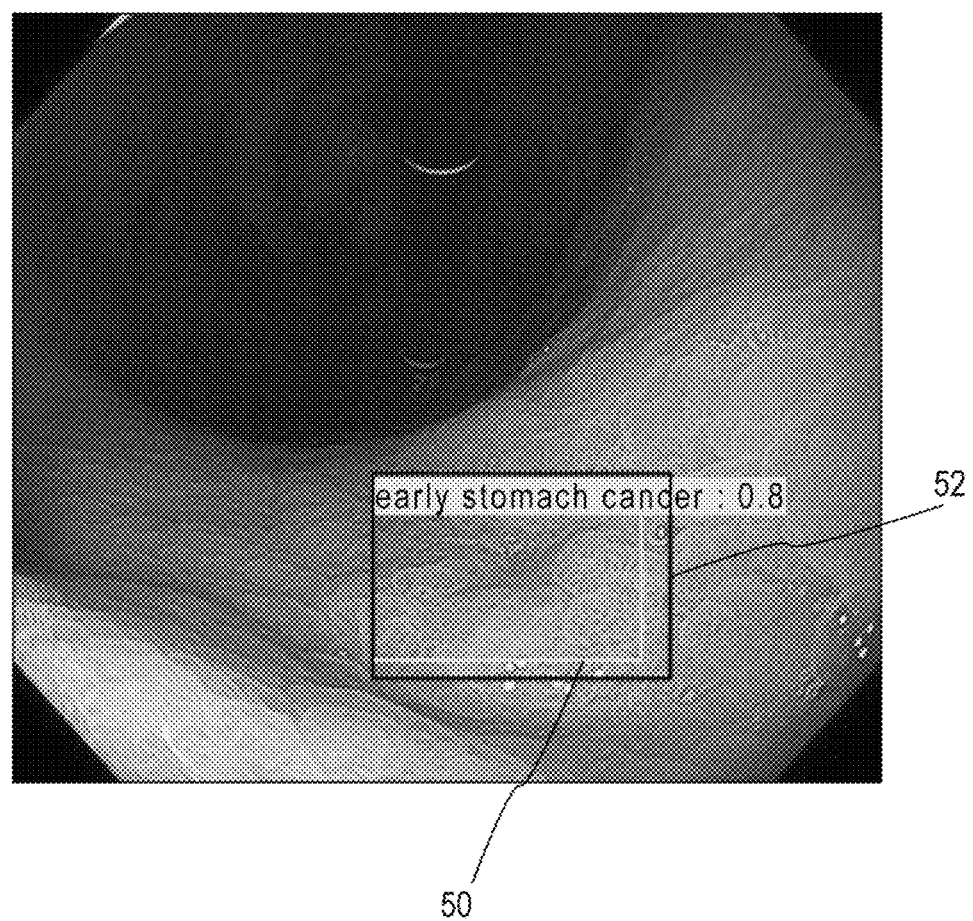
FIG. 4 is a diagram illustrating an example of an endoscopic image with an analysis result image displayed thereon according to this embodiment.

FIG. 4 is a diagram illustrating an example of an endoscopic image with an analysis result image displayed thereon according to this embodiment. As illustrated in FIG. 4, the analysis result image shows rectangular frame 50 indicating a lesion location (range) estimated by lesion estimation section 20, a lesion name (early cancer: early stomach cancer), and a probability score (0.8). In this embodiment, a rectangular frame indicating a lesion location (range) estimated by lesion estimation section 20 is displayed in yellow when the probability score is greater than or equal to a certain threshold (for example, 0.4), in order to draw attention of the doctor who refers to the analysis result image to the rectangular frame. That is, display control section 30 changes the display style of lesion-location identifying information (in this embodiment, a rectangular frame) identifying a lesion location in an analysis result image in accordance with the probability score indicated by estimation result data D2 output from lesion estimation section 20. Rectangular frame 52 indicates, for reference, a lesion location (range) diagnosed as gastric cancer by the doctor and is not displayed in the actual analysis result image, indicating that the same result as that of the determination of a well-experienced endoscopist is obtained.

[Learning Apparatus]

Learning apparatus 40 receives input of teacher data D4 stored in an external storage apparatus (not illustrated) and performs a learning process on a convolutional neural network of learning apparatus 40 so that the convolutional neural network of lesion estimation section 20 can estimate a lesion location, a lesion name, and a probability score from endoscopic image data D1.

In this embodiment, learning apparatus 40 performs a learning process using, as teacher data D4, endoscopic images of digestive organs of the subject (corresponding to "digestive-organ tumor endoscopic images" of the present invention), which are captured by endoscopic image capturing apparatus 200, and lesion names and lesion locations of lesions present in the endoscopic images, which are determined in advance by the doctor through feature extraction of atrophy, intestinal metaplasia, mucosal swelling or depression, and a condition of mucosal color tones. Specifically, learning apparatus 40 performs a learning process of the convolutional neural network so as to reduce the error (also called loss) of output data from a correct-answer value (a lesion name and a lesion location) obtained when an endoscopic image is input to the convolutional neural network.

In this embodiment, the endoscopic images used as teacher data D4 include endoscopic images captured with white light illumination on the digestive organs of the subject, endoscopic images captured with dyes (for example, indigo carmine or an iodine solution) applied to the digestive organs of the subject, and endoscopic images captured with narrow-band light (for example, NBI (Narrow Band Imaging) narrow-band light or BLI (Blue Laser Imaging) narrow-band light) illumination on the digestive organs of the subject. In the learning process, the endoscopic images used as teacher data D4 are obtained mainly from a database in a top-ranked special cancer treatment hospital in Japan, by a doctor with abundant experience of diagnosis and treatment, who is certified by the Japan Gastroenterological Endoscopy Society, examining all the images in detail, selecting images, and marking lesion locations of lesions through precise manual processing. The accuracy management of teacher data D4 (endoscopic image data), which serves as reference data, is directly connected to the analysis accuracy of diagnostic imaging support apparatus 100, and therefore image selection, lesion identification, and marking for feature extraction by an expert endoscopist having abundant experience is very important steps.

Teacher data D4 of the endoscopic images may be data of pixel values or data subjected to predetermined color conversion processing or the like. In addition, texture features, shape features, spread features, and the like extracted in pre-processing may be used. Teacher data D4 may be associated with information related to the age, gender, geographic area, or past medical history, in addition to the endoscopic image data, to perform a learning process.

Learning apparatus 40 may perform a learning process using a known algorithm. Learning apparatus 40 performs a learning process on the convolutional neural network using, for example, known backpropagation to adjust network parameters (such as a weight coefficient and a bias). The model data (such as structured data and learned weight parameters) of the convolutional neural network on which a learning process is performed by learning apparatus 40 is stored in external storage apparatus 104 together with, for example, the diagnostic imaging support program.

As described above in detail, in this embodiment, diagnostic imaging support apparatus 100 includes a lesion estimation section that estimates a name and a location of a lesion present in a digestive-organ endoscopic image of a subject and information on certainty of the name and the location of the lesion using a convolutional neural network, the digestive-organ endoscopic image being captured by a digestive-organ endoscopic image capturing apparatus, and a display control section that performs control to generate an analysis result image showing the name and the location of the lesion and the certainty of the name and the location of the lesion and to display the analysis result image on the digestive-organ endoscopic image. The convolutional neural network is subjected to a learning process based on lesion names and lesion locations of lesions present in a plurality of digestive-organ tumor endoscopic images, the lesion names and the lesion locations of the lesions being determined in advance through feature extraction of atrophy, intestinal metaplasia, mucosal swelling or depression, and a condition of mucosal color tones.

According to this embodiment with the configuration described above, a convolutional neural network is learned based on a plurality of endoscopic images of digestive organs, which are obtained in advance for each of a plurality of subjects, and based on determined diagnostic results of lesion names and lesion locations of lesions obtained in advance for each of the plurality of subjects. Thus, lesion names and lesion locations in digestive organs of a new subject can be estimated for a short time with accuracy substantially comparable to that of an experienced endoscopist. In endoscopy of the digestive organs, therefore, it is possible to strongly support an endoscopist in diagnosis based on endoscopic images by using the diagnostic endoscopic imaging capability of the convolutional neural network of the present invention. In the actual clinical situation, the endoscopist is able to use the convolutional neural network directly as a diagnostic support tool in a consulting room, and is also able to use endoscopic images transmitted from a plurality of consulting rooms for a central diagnostic support service or perform remote control via an Internet line to use a diagnostic support service for an organization in a remote location.

The embodiment described above merely provides specific examples to carry out the present invention, and such examples should not construe the technical scope of the present invention in a restrictive manner. That is, the present invention can be carried out in various forms without departing from the gist or main features thereof.

[Experimental Example]

Finally, an assessment test for determining advantageous effects achieved with the configuration of the embodiment described above will be described.

[Preparation of Learning Data Sets]

Endoscopic images from EGD performed from April 2004 to December 2016 were prepared as learning data sets (teacher data) to be used for learning a convolutional neural network in a diagnostic imaging support apparatus. EGD was performed for screening in daily clinical practice or preoperative examination, and the endoscopic images were collected using standard endoscopes (GIF-H290Z, GIF-H290, GIF-XP290N, GIF-H260Z, GIF-Q260J, GIF-XP260, GIF-XP260NS, GIF-N260, etc., Olympus Medical Systems Corp., Tokyo) and standard endoscopic video systems (EVIS LUCERA CV-260/CLV-260, and EVIS LUCERA ELITE CV-290/CLV-290SL, Olympus Medical Systems Corp.).

The endoscopic images serving as learning data sets included endoscopic images captured with white light illumination on the digestive organs of the subject, endoscopic images captured with dyes (for example, indigo carmine or an iodine solution) applied to the digestive organs of the subject, and endoscopic images captured with narrow-band light (for example, NBI narrow-band light or BLI narrow-band light) illumination on the digestive organs of the subject. Endoscopic images with poor image quality due to poor expansion of the stomach caused by insufficient air supply, bleeding after biopsy, halation, fogging of lens, defocusing, mucus, or the like were excluded from the learning data sets.

Finally, 13,584 endoscopic images for 2,639 histologically proven gastric cancers were collected as learning data sets. A doctor who was a gastric cancer specialist and was certified by the Japan Gastroenterological Endoscopy Society (with 10 years of experience at a cancer specialist hospital and with experience of diagnosis of gastric cancers in 6,000 or more cases) performed the precise manual setting of marking for feature extraction on the lesion names and lesion locations of all gastric cancers (early cancer or advanced cancer) in the collected endoscopic images, and prepared learning data sets.

[Learning/Algorithm]

To construct a diagnostic imaging support apparatus, a convolutional neural network based on VGG (https://arxiv.org/abs/1409.1556) and constituted by 16 or more layers was used. The Caffe deep learning framework, which was developed in Berkeley Vision and Learning Center (BVLC), was used for learning and an assessment test. All the layers of the convolutional neural network are finely adjusted with a global learning rate of 0.0001 by using the stochastic gradient descent method. To ensure compatibility with CNN, each image was resized to 300×300 pixels.

[Preparation of Assessment Test Data Sets]

To assess the diagnostic accuracy of the constructed convolutional-neural-network-based diagnostic imaging support apparatus, 2,296 endoscopic images (stomach) for 69 patients (77 lesions of gastric cancer) who underwent EGD as a normal clinical examination at the Cancer Institute Hospital of JFCR in Ariake from Mar. 1, 2017 to Mar. 31, 2017 were collected as assessment test data sets. As a result, 1 lesion of gastric cancer was present in 62 patients, 2 lesions of gastric cancer were present in 6 patients, and 3 lesions of gastric cancer were present in 1 patient. All the EGD procedures were performed using a standard endoscope (GIF-H290Z, Olympus Medical Systems Corp., Tokyo) and a standard endoscopic video systems (EVIS LUCERA ELITE CV-290/CLV-290SL, Olympus Medical Systems Corp.). In EGD, with observation through the stomach, endoscopic images were captured. The number of captured images was 18 to 69 per patient.

FIG. 5 is a diagram illustrating features of patients and lesions related to endoscopic images used for assessment test data sets. As illustrated in FIG. 5, the median of the tumor sizes (diameters) was 24 mm, and the range of the tumor sizes (diameters) was 3 to 170 mm In macroscopic classification, there were 55 lesions (71.4%) of the superficial type (0-IIa, 0-IIb, 0-IIc, 0-IIa+IIc, 0-IIc+IIb, and 0-IIc+III), the number of which was the largest. In terms of tumor depth, there were 52 lesions (67.5%) of early gastric cancer (T1), and 25 lesions (32.5%) of advanced gastric cancer (T2-T4).

[Method for Assessment Test]

In this assessment test, assessment test data sets were input to a diagnostic imaging support apparatus based on a convolutional neural network on which a learning process was performed using learning data sets, and it was assessed whether gastric cancer was correctly detected from each of the endoscopic images constituting the assessment test data sets. A correct detection of gastric cancer was regarded as a "correct answer". Upon detection of a gastric cancer (lesion) from the endoscopic images, the convolutional neural network outputs the lesion name (early gastric cancer or advanced gastric cancer), the lesion location, and the probability score.

Among gastric cancers present in the endoscopic images constituting the assessment test data sets, several gastric cancers were present in a plurality of endoscopic images. Thus, the assessment test was conducted using the following definitions.

(Definition 1)

Figure 6A:
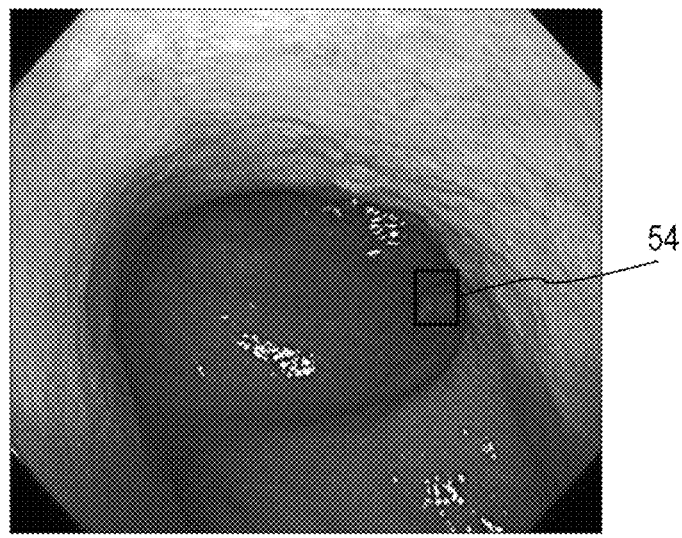
FIGS. 6A and 6B are diagrams illustrating an example of endoscopic images and an analysis result image.
Figure 6B:
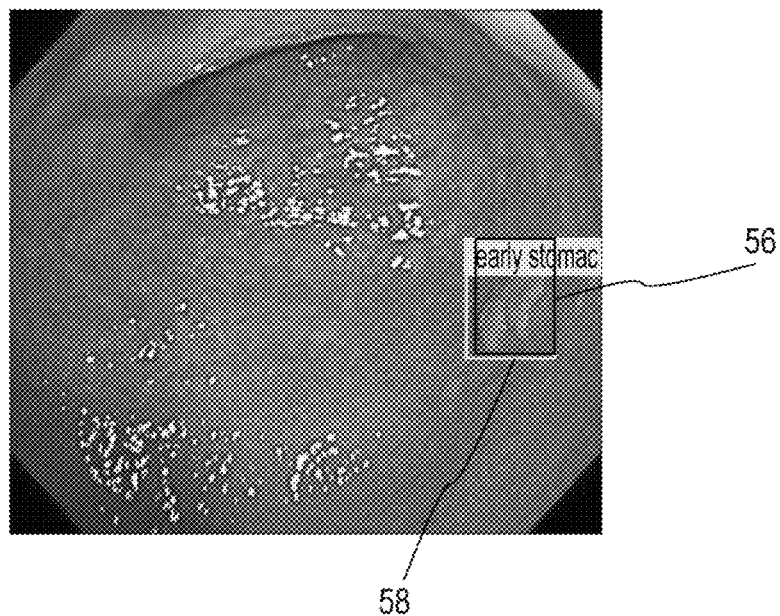

When the convolutional neural network detected the same (one) gastric cancer in a plurality of endoscopic images, this case was regarded as a correct answer. FIGS. 6A and 6B are diagrams describing the presence of the same cancer in a plurality of endoscopic images. In FIGS. 6A and 6B, rectangular frames 54 and 56 indicate lesion locations (ranges) of gastric cancer, which were manually set by the doctor. Rectangular frame 58 indicates a lesion location (range) of gastric cancer, which was estimated by the convolutional neural network. FIG. 6A illustrates an endoscopic image in which gastric cancer was shown in background, and FIG. 6B illustrates an endoscopic image in which the gastric cancer was within the near field of view. As illustrated in FIGS. 6A and 6B, the convolutional neural network failed to detect gastric cancer in background, whereas the convolutional neural network was successful in detecting gastric cancer in foreground. This case was regarded as a correct answer in this assessment test.

(Definition 2)

When false-positive lesions (gastric cancers) detected in different endoscopic images were the same lesion, these lesions were regarded as a single lesion.

(Definition 3)

Figure 7:
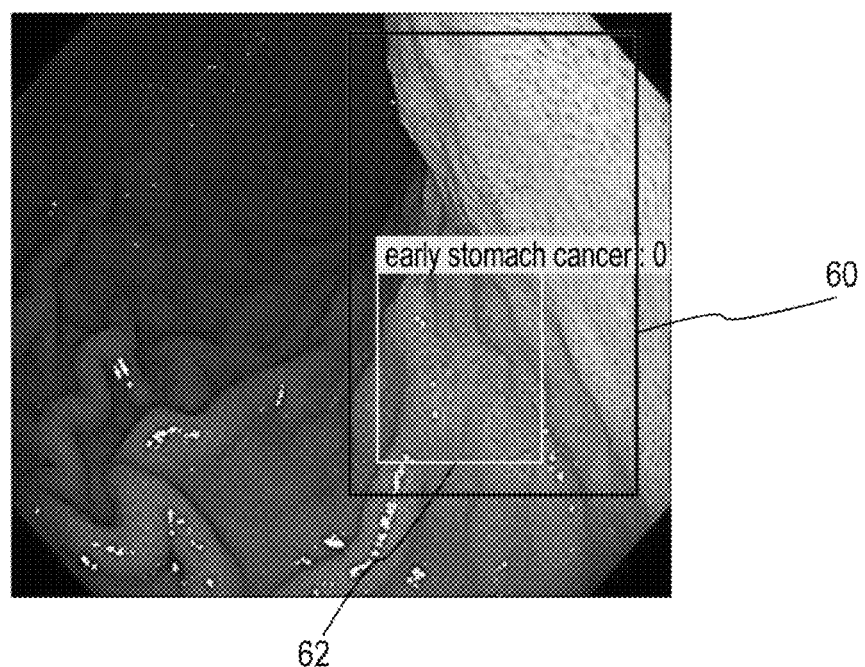
FIG. 7 is a diagram describing a difference between a lesion location (range) diagnosed by a doctor and a lesion location (range) diagnosed by the convolutional neural network.

In some cases, the boundary of a lesion location (range) of gastric cancer is unclear. Thus, when a portion of gastric cancer was detected by the convolutional neural network, this case was regarded as a correct answer. FIG. 7 is a diagram describing a difference between a lesion location (range) diagnosed by the doctor and a lesion location (range) diagnosed by the convolutional neural network. In FIG. 7, rectangular frame 60 indicates a lesion location (range) of gastric cancer, which was manually set by the doctor. Rectangular frame 62 indicates a lesion location (range) of gastric cancer, which was estimated by the convolutional neural network. As illustrated in FIG. 7, there was a difference between the lesion location (range) of gastric cancer, which was manually set by the doctor, and the lesion location (range) of gastric cancer, which was estimated by the convolutional neural network. In this manner, when at least a portion of gastric cancer was detected by the convolutional neural network, this case was regarded as a correct answer in this assessment test.

In this assessment test, furthermore, the sensitivity and positive predictive value (PPV) for the diagnostic capability of the convolutional neural network to detect gastric cancer were calculated using following equations 1 and 2.

$$\text{Sensitivity} = \text{(the number of gastric cancers detected by the convolutional neural network)} / \text{(the number of gastric cancers (77) present in the endoscopic images constituting the assessment test data sets)} \quad \text{(Equation 1)}$$

$$\text{Positive predictive value} = \text{(the number of gastric cancers detected by the convolutional neural network)} / \text{(the number of lesions diagnosed as gastric cancer by the convolutional neural network)} \quad \text{(Equation 2)}$$

[Results of Assessment Test]

The convolutional neural network finished a process for analyzing the 2,296 endoscopic images constituting the assessment test data sets in as short a time as 47 seconds. In addition, the convolutional neural network detected 71 gastric cancers out of 77 gastric cancers (lesions). That is, the sensitivity for the diagnostic capability of the convolutional neural network was 92.2%.

Figure 8A:
FIGS. 8A and 8B are diagrams illustrating an example of an endoscopic image and an analysis result image.
Figure 8B:
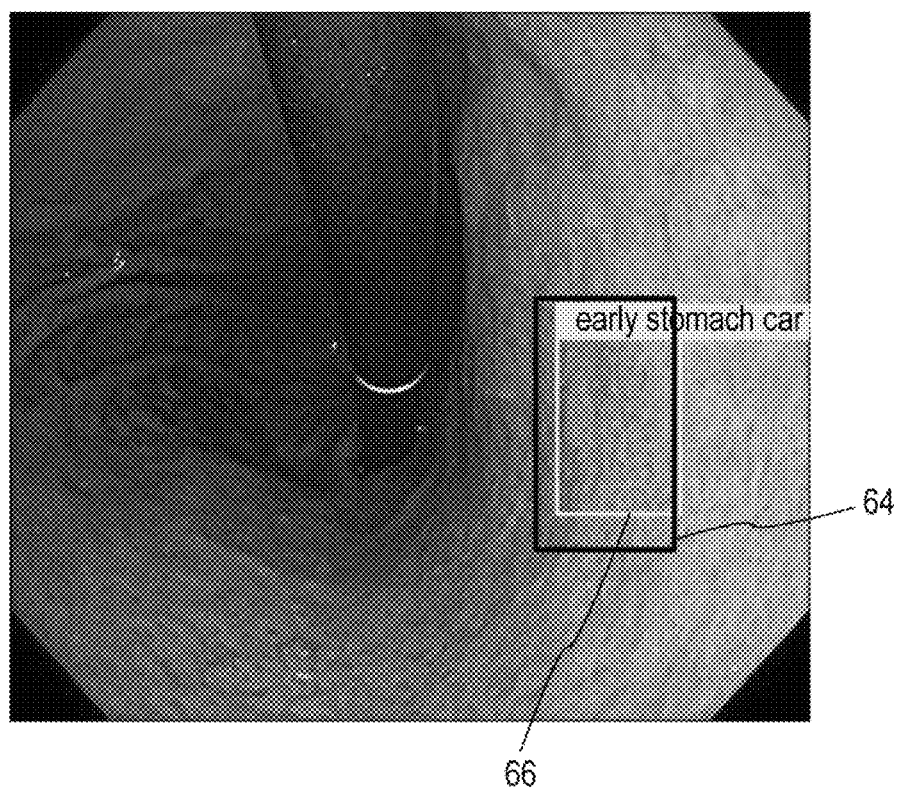

FIGS. 8A and 8B are diagrams illustrating an example of an endoscopic image and an analysis result image. FIG. 8A illustrates an endoscopic image in which a flat, slightly red lesion is represent over the lesser curvature of the middle gastric corpus. Since gastric cancer resembles atrophy of the background mucosa, it seemed to be difficult for even an endoscopist to detect gastric cancer from the endoscopic image in FIG. 8A. FIG. 8B illustrates an analysis result image indicating that the convolutional neural network was successful in detecting gastric cancer (0-IIc, 5 mm, tub1, T1a). In FIG. 8B, rectangular frame 64 indicates a lesion location (range) of gastric cancer, which was manually set by the doctor. Rectangular frame 66 indicates a lesion location (range) of gastric cancer, which was estimated by the convolutional neural network.

FIG. 9 is a diagram illustrating a change in sensitivity depending on different tumor depths and tumor sizes in this assessment test. As illustrated in FIG. 9, the convolutional neural network detected 70 gastric cancers (98.6%) out of 71 gastric cancan whose tumor sizes (diameters) were 6 mm or more. In addition, the convolutional neural network was successful in detecting all invasive cancers (T1b, T2, T3, and T4a).

On the other hand, the convolutional neural network missed six gastric cancers. Five out of the six gastric cancers were very small cancers (tumor sizes≤5 mm). All the missed gastric cancers were differentiated intramucosal carcinomas, which were difficult for even an endoscopist to distinguish from gastritis. Since the doubling time (the period of time taken for a tumor to double in volume) of gastric intramucosal carcinoma is considered to be two to three years, even if such a small cancer is missed, the cancer is considered to be detected as intramucosal carcinoma by EGD each year, which does not hinder the usability and clinical application of the convolutional neural network of the present invention.

FIG. 10 is a diagram illustrating the details of lesions (gastric cancers) missed by the convolutional neural network. FIGS. 11A, 11B, 11C, 11D, 11E, and 11F are diagrams illustrating endoscopic images (analysis result images) in which lesions missed by the convolutional neural network are present.

Figures 11A, 11B, 11C:
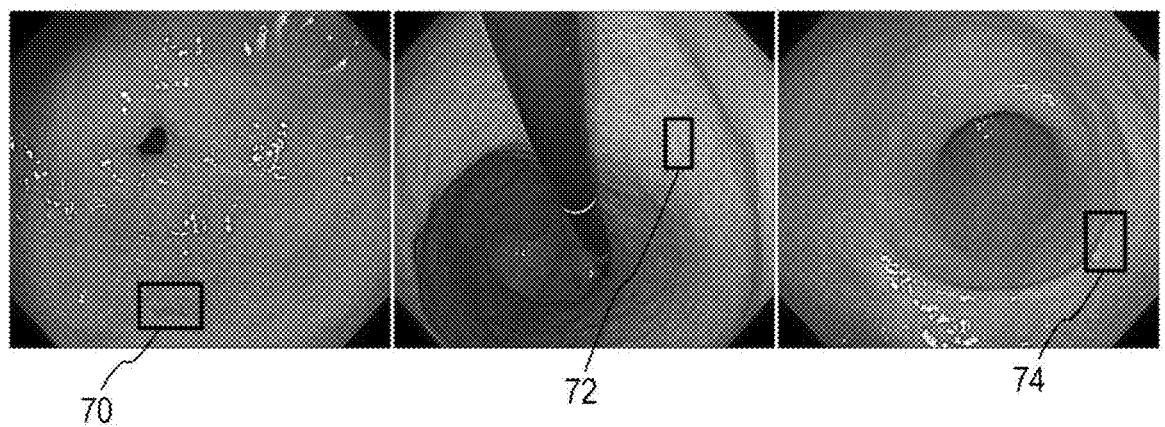
FIGS. 11A, 11B, 11C, 11D, 11E, and 11F are diagrams illustrating endoscopic images in which lesions missed by the convolutional neural network are present.

In FIG. 11A, rectangular frame 70 indicates a lesion location (range) of gastric cancer (the antral greater curvature, 0-IIc, 3 mm, tub1, T1a), which was missed by the convolutional neural network. In FIG. 11B, rectangular frame 72 indicates a lesion location (range) of gastric cancer (the lesser curvature of the middle gastric corpus, 0-IIc, 4 mm, tub1, T1a), which was missed by the convolutional neural network.

Figures 11D, 11E, 11F:
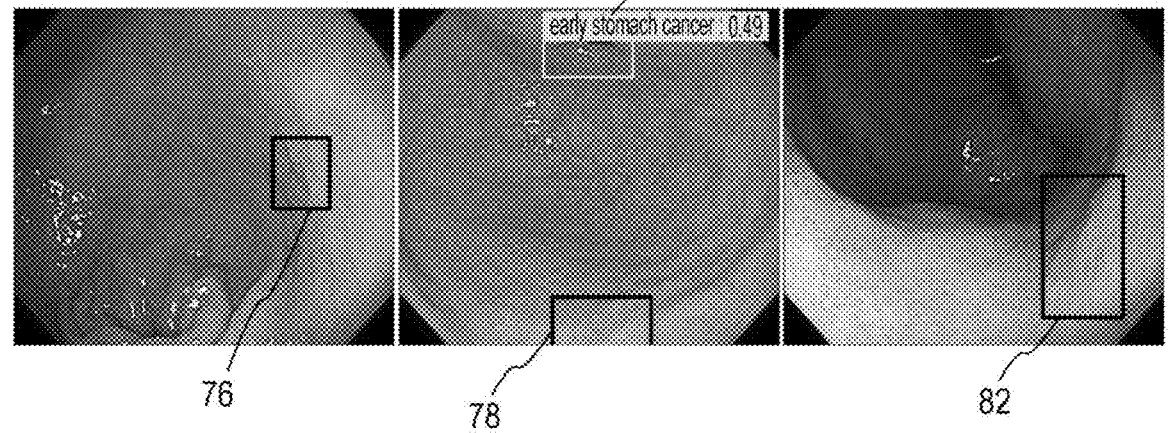

In FIG. 11C, rectangular frame 74 indicates a lesion location (range) of gastric cancer (the antral posterior wall, 0-IIc, 4 mm, tub1, T1a), which was missed by the convolutional neural network. In FIG. 11D, rectangular frame 76 indicates a lesion location (range) of gastric cancer (the antral posterior wall, 0-IIc, 5 mm, tub1, T1a), which was missed by the convolutional neural network.

In FIG. 11E, rectangular frame 78 indicates a lesion location (range) of gastric cancer (the antral greater curvature, 0-IIc, 5 mm, tub1, T1a), which was missed by the convolutional neural network. Rectangular frame 80 indicates a noncancerous lesion (pylorus) estimated as gastric cancer by the convolutional neural network. In FIG. 11F, rectangular frame 82 indicates a lesion location (range) of gastric cancer (the anterior wall of the lower gastric corpus, 0-IIc, 16 mm, tub1, T1a), which was missed by the convolutional neural network.

In addition, the convolutional neural network detected 161 noncancerous lesions as gastric cancer. The positive predictive value was 30.6%. FIG. 12 is a diagram illustrating the details of noncancerous lesions detected as gastric cancer by the convolutional neural network. As illustrated in FIG. 12, substantially half of the noncancerous lesions detected as gastric cancer were gastritis with changes in color or irregular changes in mucosal surface. Such gastritis is difficult for an endoscopist to distinguish from gastric cancer in many cases, and the positive predictive value (PPV) of gastric cancer diagnosis via gastric biopsy is reported to be 3.2 to 5.6%. For clinical diagnosis of cancer, failure to detect cancer leads to the loss of the opportunity to treat the patient. Accordingly, the severity of false-negative errors is greater than that of false-positive errors. In view of low PPV of biopsies performed by the endoscopist, the PPV of the convolutional neural network is considered to be clinically sufficiently acceptable.

Figure 13A:
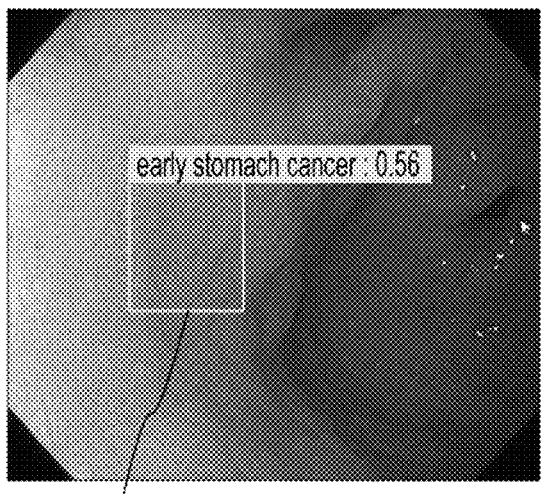
FIGS. 13A, 13B, and 13C are diagrams illustrating analysis result images containing noncancerous lesions detected as gastric cancer by the convolutional neural network.
Figure 13B:
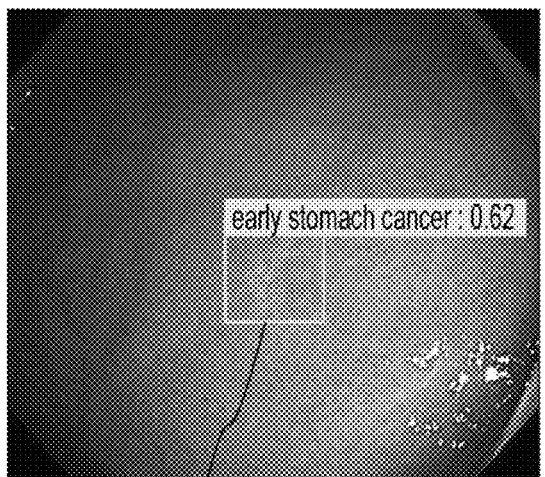
Figure 13C:
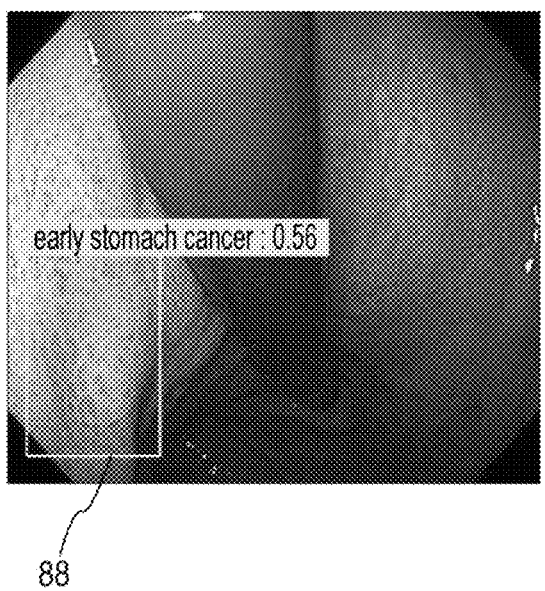

FIGS. 13A, 13B, and 13C are diagrams illustrating analysis result images containing noncancerous lesions detected as gastric cancer by the convolutional neural network. In FIG. 13A, rectangular frame 84 indicates a lesion location (range) of gastritis (intestinal metaplasia with irregular mucosal surface structure) detected as gastric cancer by the convolutional neural network. In FIG. 13B, rectangular frame 86 indicates a lesion location (range) of gastritis (white mucosa due to local atrophy) detected as gastric cancer by the convolutional neural network. In FIG. 13C, rectangular frame 88 indicates a lesion location (range) of gastritis (redness of the mucosa caused by chronic gastritis) detected as gastric cancer by the convolutional neural network.

Next, a second assessment test for determining advantageous effects achieved with the configuration of the embodiment described above will be described.

[Preparation of Learning Data Sets]

Endoscopic images of 12,895 examples of endoscopy of the large intestine, which was performed from December 2013 to March 2017, were prepared as learning data sets (teacher data) to be used for learning a convolutional neural network in a diagnostic imaging support apparatus. The endoscopic images contain adenocarcinoma, adenoma, hyperplastic polyp, SSAP (sessile serrated adenoma/polyps), juvenile polyp, Peutz-Jeghers polyp, inflammatory polyp, lymphoid aggregate, and so on, which were histologically proven by a certified pathologist. EGD was performed for screening in daily clinical practice or preoperative examination, and the endoscopic images were collected using standard endoscopic video systems (EVIS LUCERA: CF TYPE H260AL/I, PCF TYPE Q260AI, Q260AZI, H290I, H290Z, Olympus Medical Systems Corp.).

Figure 14A:
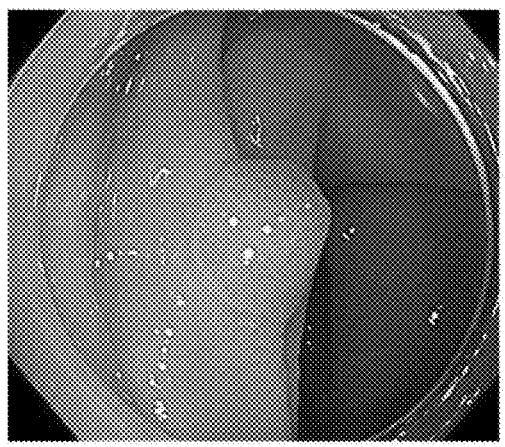
FIGS. 14A, 14B, 14C, 14D, 14E, and 14F are diagrams illustrating endoscopic images of the large intestine that contain adenoma, hyperplastic polyp, or SSAP.
Figure 14B:
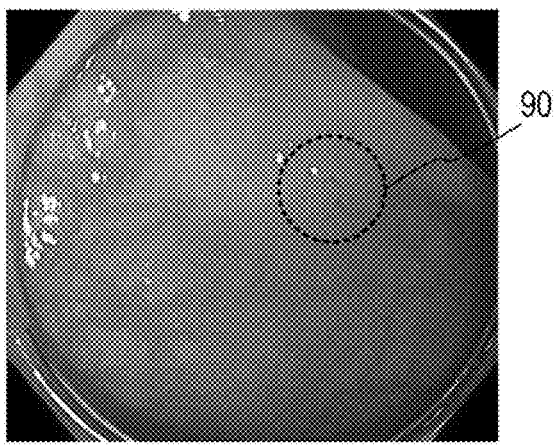
Figure 14C:
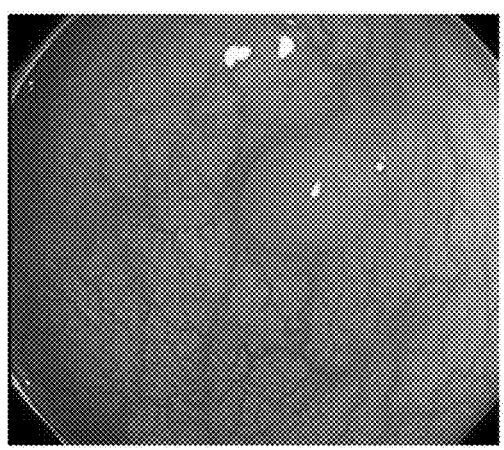
Figure 14D:
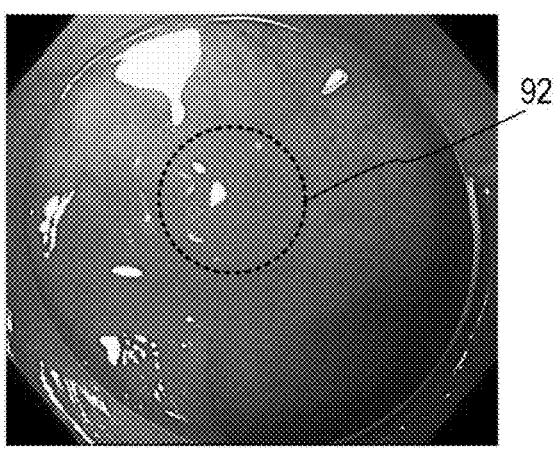
Figure 14E:
Figure 14F:
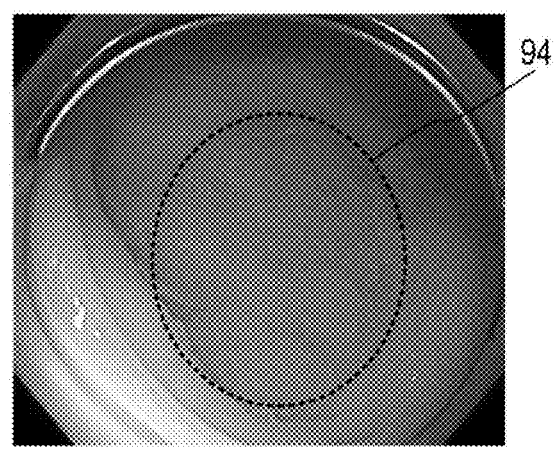

FIG. 14A illustrates an endoscopic image of the large intestine that contains protruding adenoma. FIG. 14B illustrates an endoscopic image of the large intestine that contains a flat tumor (see dotted line 90). FIG. 14C illustrates an endoscopic image of the large intestine that contains protruding hyperplastic polyp. FIG. 14D illustrates an endoscopic image of the large intestine that contains flat hyperplastic polyp (see dotted line 92). FIG. 14E illustrates an endoscopic image of the large intestine that contains protruding SSAP. FIG. 14F illustrates an endoscopic image of the large intestine that contains flat SSAP (see dotted line 94).

The endoscopic images serving as learning data sets included endoscopic images captured with white light illumination on the large intestine of the subject, and endoscopic images captured with narrow-band light (for example, NBI narrow-band light) illumination on the large intestine of the subject. Endoscopic images with poor image quality due to fecal residue, halation, or bleeding after biopsy were excluded from the learning data sets.

Figure 15A:
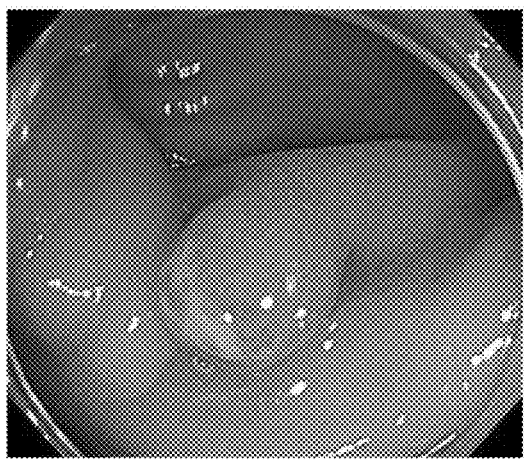
FIGS. 15A, 15B, 15C, 15D, 15E, and 15F are diagrams illustrating endoscopic images of the large intestine that contain rare types of colorectal polyps.
Figure 15B:
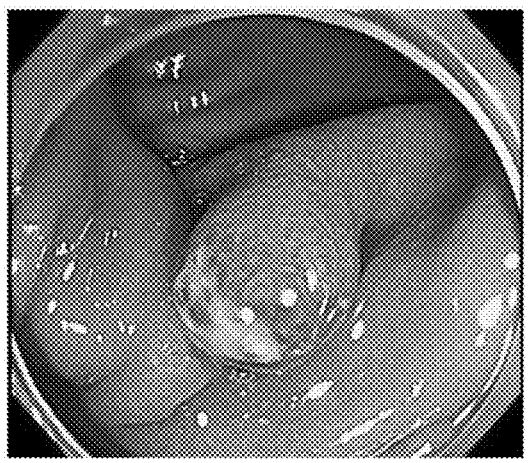
Figure 15C:
Figure 15D:
Figure 15E:
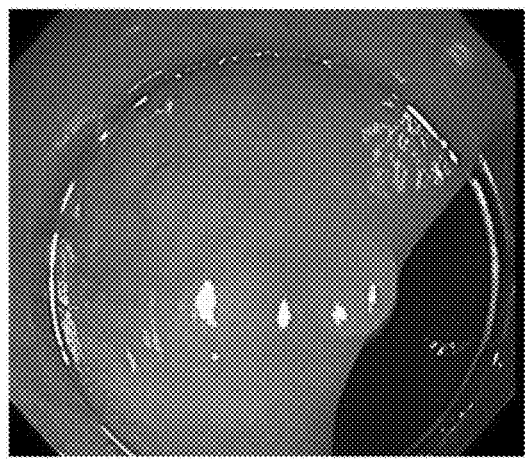
Figure 15F:
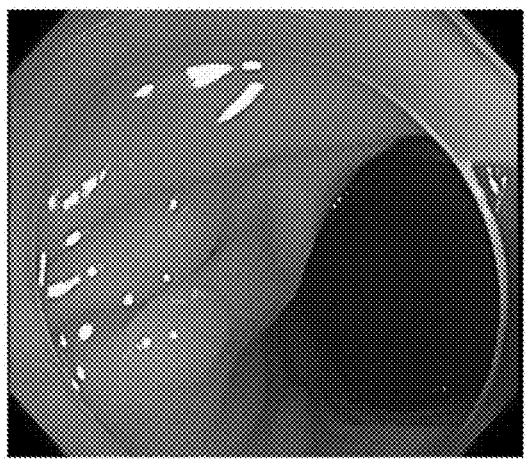

FIG. 15A illustrates an endoscopic image captured with white light illumination on a Peutz-Jeghers polyp in the large intestine of the subject. FIG. 15B illustrates an endoscopic image captured with narrow-band light (NBI narrow-band light) illumination on the Peutz-Jeghers polyp in the large intestine of the subject. FIG. 15C illustrates an endoscopic image captured with white light illumination on an inflammatory polyp in the large intestine of the subject. FIG. 15D illustrates an endoscopic image captured with narrow-band light (NBI narrow-band light) illumination on the inflammatory polyp in the large intestine of the subject. FIG. 15E illustrates a captured endoscopic image of a non-neoplastic mucosa that looks like a polypoid area in the large intestine of the subject. FIG. 15F illustrates a captured endoscopic image of a lymphocyte aggregate that looks like a polypoid area in the large intestine of the subject.

Finally, 20,431 endoscopic images for 4,752 histologically proven colorectal polyps were collected as learning data sets, and 4,013 endoscopic images for normal colonic mucosa were collected. In the collected endoscopic images, the precise manual setting of marking for feature extraction was performed on the lesion names (types) and lesion locations of all colorectal polyps. FIG. 16 is a diagram illustrating features of colorectal polyps and the like related to endoscopic images used for learning data sets. In FIG. 16, if a single endoscopic image contained a plurality of colorectal polyps, each of the plurality of colorectal polyps was counted as a different endoscopic image.

[Learning/Algorithm]

To construct a diagnostic imaging support apparatus, a convolutional neural network based on a Single Shot MultiBox Detector (SSD, https://arxiv.org/abs/1512.02325) and constituted by 16 or more layers was used. The Caffe deep learning framework, which was developed in Berkeley Vision and Learning Center (BVLC), was used for learning and an assessment test. All the layers of the convolutional neural network are finely adjusted with a global learning rate of 0.0001 by using the stochastic gradient descent method. To ensure compatibility with CNN, each image was resized to 300×300 pixels. In accordance with the resizing of each image, the marking size was changed for the lesion location of the lesion.

[Preparation of Assessment Test Data Sets]

To assess the diagnostic accuracy of the constructed convolutional-neural-network-based diagnostic imaging support apparatus, 6,759 endoscopic images (large intestine) for 174 patients who underwent EGD as a normal clinical examination from Jan. 1, 2017 to Mar. 31, 2017, including 885 endoscopic images having colorectal polyps, were collected as assessment test data sets. To assess the diagnostic accuracy of the diagnostic imaging support apparatus in normal clinical examination, endoscopic images with fecal contamination or related to insufficient air supply were also collected as assessment test data sets. However, endoscopic images with inflammatory bowel disease were excluded from the assessment test data sets since the diagnostic result could change. In addition, endoscopic images with bleeding after biopsy and endoscopic images after endoscopic treatment were also excluded from the assessment test data sets. The endoscopic images used as the assessment test data sets included, like the learning data sets, endoscopic images captured with white light illumination on the large intestine of the subject, and endoscopic images captured with narrow-band light (for example, NBI narrow-band light) illumination on the large intestine of the subject. FIG. 17 is a diagram illustrating features of colorectal polyps and the like related to endoscopic images used for assessment test data sets. In FIG. 17, if a single endoscopic image contained a plurality of colorectal polyps, each of the plurality of colorectal polyps was counted as a different endoscopic image.

[Method for Assessment Test]

In this assessment test, assessment test data sets were input to a diagnostic imaging support apparatus based on a convolutional neural network on which a learning process was performed using learning data sets, and it was assessed whether a colorectal polyp was correctly detected from each of the endoscopic images constituting the assessment test data sets. A correct detection of a colorectal polyp was regarded as a "correct answer". Upon detection of a colorectal polyp from the endoscopic images, the convolutional neural network outputs the lesion name (type), the lesion location, and the probability score.

To acquire results of the assessment test, the assessment test was conducted using the following definitions.

(Definition 1)

In this assessment test, if a lesion location (range) of a colorectal polyp diagnosed by the convolutional neural network overlapped an area corresponding to 80% or more of a lesion location (range) of a colorectal polyp diagnosed by the doctor, it was determined that the convolutional neural network correctly detected a colorectal polyp from an endoscopic image, and this case was regarded as a correct answer.

(Definition 2)

In this assessment test, if the convolutional neural network detected two or more colorectal polyps of different types from an endoscopic image as the same lesion location (range), it was determined that the convolutional neural network detected a colorectal polyp of the type having the highest probability score.

In this assessment test, furthermore, the sensitivity and positive predictive value (PPV) for the diagnostic capability of the convolutional neural network to detect a colorectal polyp were calculated using following equations 1 and 2.

$$\text{Sensitivity} = \frac{\text{(the number of colorectal polyps detected by the convolutional neural network)}}{\text{(the number of colorectal polyps present in the endoscopic images constituting the assessment test data sets)}} \quad \text{(Equation 1)}$$

$$\text{Positive predictive value} = \frac{\text{(the number of colorectal polyps detected by the convolutional neural network)}}{\text{(the number of lesions diagnosed as colorectal polyps by the convolutional neural network)}} \quad \text{(Equation 2)}$$

[Results of Assessment Test]

The convolutional neural network finished a process for analyzing the endoscopic images constituting the assessment test data sets at as high a speed as 48.7 images/second (i.e., the analysis processing time per endoscopic image: 20 ms). In addition, the convolutional neural network estimated the lesion locations of 1,247 colorectal polyps in the endoscopic images constituting the assessment test data sets, and correctly detected 1,073 colorectal polyps out of 1,172 true (histologically proven) colorectal polyps. The sensitivity and the positive predictive value for the diagnostic capability of the convolutional neural network were 92% and 86%, respectively.

Specifically, in endoscopic images captured with white light illumination on the large intestine of the subject, the sensitivity and the positive predictive value for the diagnostic capability of the convolutional neural network were 90% and 82%, respectively. In endoscopic images captured with narrow-band light (NBI narrow-band light) illumination on the large intestine of the subject, the sensitivity and the positive predictive value for the diagnostic capability of the convolutional neural network were 97% and 98%, respectively.

Further, the convolutional neural network estimated the lesion locations of 1,143 colorectal polyps in the endoscopic images constituting the assessment test data sets (including true colorectal polyps only less than 10 mm), and correctly detected 969 colorectal polyps out of the 1,143 true colorectal polyps. The sensitivity and the positive predictive value for the diagnostic capability of the convolutional neural network were 92% and 85%, respectively.

To improve the diagnostic capability of the convolutional neural network, it is important to identify the reason that the convolutional neural network failed to correctly detect true colorectal polyps, that is, the convolutional neural network missed the true colorectal polyps. Accordingly, the present inventors have reviewed all of the endoscopic images (false-positive images) in which colorectal polyps were incorrectly detected by the convolutional neural network and all of the endoscopic images (false-negative images) in which true colorectal polyps were not detected by the convolutional neural network, and classified the images into several categories.

FIG. 18 is a diagram illustrating classification results of false-positive images and false-negative images. As illustrated in FIG. 18, among 165 false-positive images, 64 false-positive images (39%) showed normal structures easily distinguishable from colorectal polyps, the majority of which were images of the ileocecal valve (N=56). Further, 55 false-positive images (33%) showed colonic folds, the majority of which were images related to insufficient air supply. Other false-positive images (20%) contained artificially generated anomaly images easily distinguishable from true colorectal polyps and caused by halation (N=14), fogging of the camera lens surface (N=4), a blur, a blur (N=2), or feces (N=4). Further, 12 false-positive images (7%) were suspected to be true polyps, but not finally confirmed.

As illustrated in FIG. 18, furthermore, in 50 false-negative images (56%) among 89 false-negative images, the colorectal polyps are considered not to have been detected as true colorectal polyps by the convolutional neural network since the colorectal polyps were small or dark so that the texture of the surfaces of the colorectal polyps was less recognizable. Further, in 34 false-negative images (38%), the colorectal polyps are considered not to have been detected as true colorectal polyps by the convolutional neural network since the colorectal polyps were captured from either side or portions thereof were captured. Further, in 5 false-negative images (6%), the colorectal polyps are considered not to have been detected as true colorectal polyps by the convolutional neural network since the colorectal polyps were very large.

The present inventors also have reviewed the degree of match between the classification of colorectal polyps detected and classified by the convolutional neural network (CNN classification) and the classification of histologically proven colorectal polyps (histological classification) as the classification accuracy of the convolutional neural network. FIGS. 19A and 19B are diagrams illustrating degrees of match between CNN classification and histological classification.

As illustrated in FIG. 19A, in endoscopic images captured with white light illumination on the large intestine of the subject, the classification of colorectal polyps that accounted for 83% of the total was correctly performed by the convolutional neural network. Colorectal polyps that accounted for 97% of the colorectal polyps histologically proven as adenomas were correctly classified as adenomas by the convolutional neural network. The positive predictive value and the negative predictive value for the diagnostic capability (classification capability) of the convolutional neural network were 86% and 85%, respectively. Further, colorectal polyps that accounted for 47% of the colorectal polyps histologically proven as hyperplastic polyps were correctly classified as hyperplastic polyps by the convolutional neural network. The positive predictive value and the negative predictive value for the diagnostic capability (classification capability) of the convolutional neural network were 64% and 90%, respectively. Further, many of the colorectal polyps histologically proven as SSAPs were incorrectly classified as adenomas (26%) or hyperplastic polyps (52%) by the convolutional neural network.

As illustrated in FIG. 19B, in endoscopic images captured with narrow-band light (NBI narrow-band light) illumination on the large intestine of the subject, the classification of colorectal polyps that accounted for 81% of the total was correctly performed by the convolutional neural network. Colorectal polyps that accounted for 97% of the colorectal polyps histologically proven as adenomas were correctly classified as adenomas by the convolutional neural network. The positive predictive value and the negative predictive value for the diagnostic capability (classification capability) of the convolutional neural network were 83% and 91%, respectively.

The present inventors also have reviewed, for colorectal polyps of 5 mm or less, the degree of match between the classification of colorectal polyps detected and classified by the convolutional neural network (CNN classification) and the classification of histologically proven colorectal polyps (histological classification) as the classification accuracy of the convolutional neural network. FIG. 20 is a diagram illustrating degrees of match between CNN classification and histological classification for colorectal polyps of 5 mm or less.

As illustrated in FIG. 20, in endoscopic images captured with white light illumination on the large intestine of the subject, colorectal polyps (N=348) that accounted for 98% of the colorectal polyps histologically proven as adenomas (N=356) were correctly classified as adenomas by the convolutional neural network. The positive predictive value and the negative predictive value for the diagnostic capability (classification capability) of the convolutional neural network were 85% and 88%, respectively. Further, colorectal polyps that accounted for 50% of the colorectal polyps histologically proven as hyperplastic polyps were correctly classified as hyperplastic polyps by the convolutional neural network. The positive predictive value and the negative predictive value for the diagnostic capability (classification capability) of the convolutional neural network were 77% and 88%, respectively. Further, although not illustrated, in endoscopic images captured with narrow-band light (NBI narrow-band light) illumination on the large intestine of the subject, colorectal polyps (N=138) that accounted for 97% of the colorectal polyps histologically proven as adenomas (N=142) were correctly classified as adenomas by the convolutional neural network. The positive predictive value and the negative predictive value for the diagnostic capability (classification capability) of the convolutional neural network were 84% and 88%, respectively. The results illustrated in FIGS. 19A, 19B, and 20 apparently indicate that the diagnostic capabilities (classification capabilities) of the convolutional neural network are the same regardless of the sizes of the colorectal polyps.

As indicated from the results of the second assessment test described above, the convolutional neural network effectively detects a colorectal polyp with considerable accuracy at a remarkable speed even if the colorectal polyp is small, and is likely to be useful to reduce failure of detection of colorectal polyps in endoscopy of the large intestine. It is also indicated that the convolutional neural network is able to correctly classify detected colorectal polyps and strongly support an endoscopist in diagnosis based on endoscopic images.

Figure 21C:
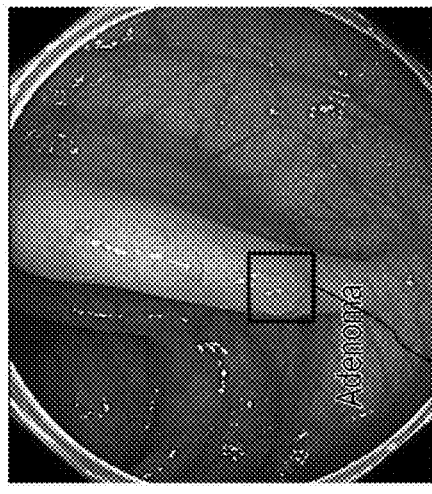
FIGS. 21A, 21B, 21C, 21D, 21E, and 21F are diagrams illustrating an example of endoscopic images and analysis result images in a second assessment test.

FIGS. 21A, 21B, 21C, 21D, 21E, and 21F and FIGS. 22A, 22B, 22C, 22D, 22E, 22F, 22G, and 22H are diagrams illustrating an example of endoscopic images and analysis result images in the second assessment test. FIG. 21A illustrates an endoscopic image and an analysis result image containing a colorectal polyp (adenoma) that was correctly detected and classified by the convolutional neural network. As illustrated in FIG. 21A, the analysis result image shows rectangular frame 110 indicating a lesion location (range) estimated by the convolutional neural network, a lesion name (adenoma: Adenoma), and a probability score (0.97). Rectangular frame 112 indicates, for reference, a lesion location (range) of a histologically proven colorectal polyp (adenoma) and is not displayed in the actual analysis result image.

Figure 21B:
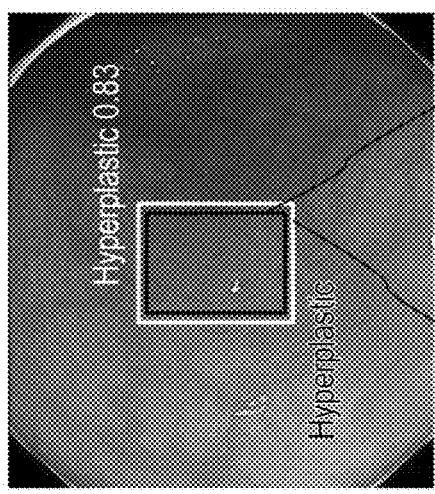
Figure 21A:
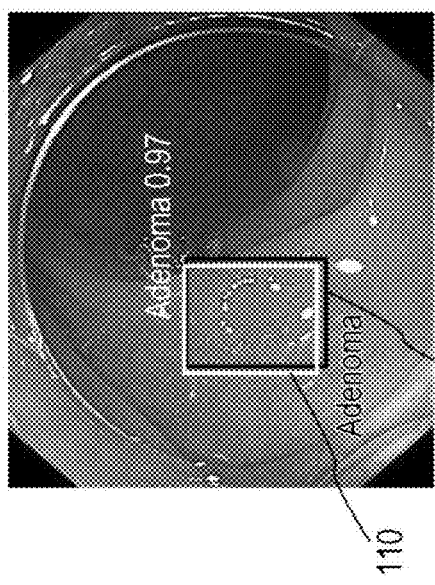

FIG. 21B illustrates an endoscopic image and an analysis result image containing a colorectal polyp (hyperplastic polyp) that was correctly detected and classified by the convolutional neural network. As illustrated in FIG. 21B, the analysis result image shows rectangular frame 114 indicating a lesion location (range) estimated by the convolutional neural network, a lesion name (hyperplastic polyp: Hyperplastic), and a probability score (0.83). Rectangular frame 116 indicates, for reference, a lesion location (range) of a histologically proven colorectal polyp (hyperplastic polyp) and is not displayed in the actual analysis result image.

FIG. 21C illustrates, as a false-negative image, an endoscopic image containing a colorectal polyp (adenoma) that was not detected, or missed, by the convolutional neural network. Rectangular frame 118 indicates, for reference, a lesion location (range) of a histologically proven colorectal polyp (adenoma) and is not displayed in the actual analysis result image.

Figure 21F:
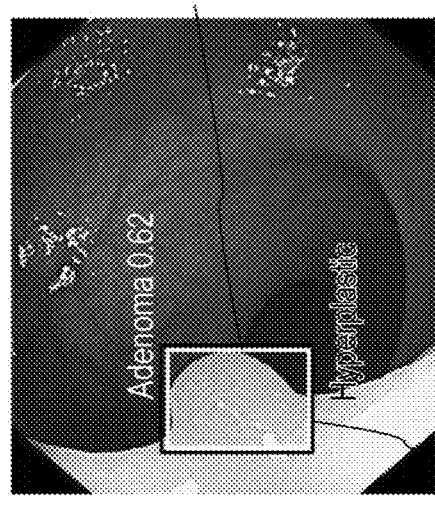
Figure 21E:
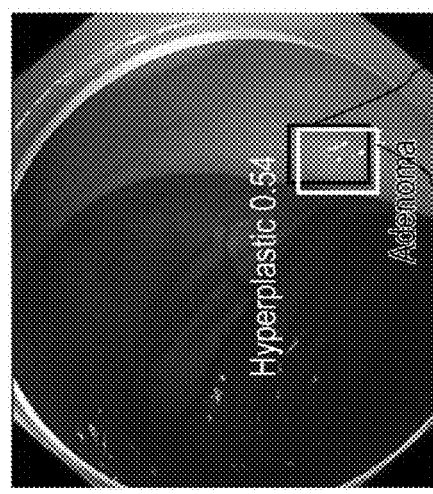
Figure 21D:
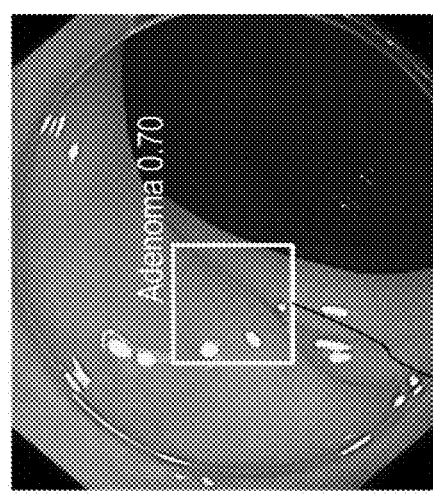

FIG. 21D illustrates, as false-positive images, an endoscopic image and an analysis result image containing a normal colonic fold that was incorrectly detected and classified by the convolutional neural network. As illustrated in FIG. 21D, the analysis result image shows rectangular frame 120 indicating a lesion location (range) estimated by the convolutional neural network, a lesion name (adenoma: Hyperplastic), and a probability score (0.70).

FIG. 21E illustrates an endoscopic image and an analysis result image containing a colorectal polyp (adenoma) whose lesion location (range) was correctly detected by the convolutional neural network, but which was incorrectly classified. As illustrated in FIG. 21E, the analysis result image shows rectangular frame 122 indicating a lesion location (range) estimated by the convolutional neural network, a lesion name (hyperplastic polyp: Hyperplastic), and a probability score (0.54). Rectangular frame 124 indicates, for reference, a lesion location (range) of a histologically proven colorectal polyp (adenoma) and is not displayed in the actual analysis result image.

FIG. 21F illustrates an endoscopic image and an analysis result image containing a colorectal polyp (hyperplastic polyp) whose lesion location (range) was correctly detected by the convolutional neural network, but which was incorrectly classified. As illustrated in FIG. 21F, the analysis result image shows rectangular frame 126 indicating a lesion location (range) estimated by the convolutional neural network, a lesion name (adenoma: Adenoma), and a probability score (0.62). A, rectangular frame 128 indicates, for reference, a lesion location (range) of a histologically proven colorectal polyp (hyperplastic polyp) and is not displayed in the actual analysis result image.

FIG. 22A illustrates, as a false-negative image, an endoscopic image containing a colorectal polyp (adenoma) that was not detected, or missed, by the convolutional neural network. Rectangular frames 130 and 132 indicate, for reference, lesion locations (ranges) of histologically proven colorectal polyps (adenomas) and are not displayed in the actual analysis result image. The colorectal polyps (adenomas) indicated by the rectangular frames 130 and 132 were very small and were less likely to be recognized. Thus, the colorectal polyps are considered not to have been detected by the convolutional neural network.

FIG. 22B illustrates, as a false-negative image, an endoscopic image containing a colorectal polyp (adenoma) that was not detected, or missed, by the convolutional neural network. Rectangular frame 134 indicates, for reference, a lesion location (range) of a histologically proven colorectal polyp (adenoma) and is not displayed in the actual analysis result image. The colorectal polyp (adenoma) indicated by the rectangular frame 134 was dark and was less likely to be recognized. Thus, the colorectal polyp is considered not to have been detected by the convolutional neural network.

FIG. 22C illustrates, as a false-negative image, an endoscopic image containing a colorectal polyp (adenoma) that was not detected, or missed, by the convolutional neural network. Rectangular frame 136 indicates, for reference, a lesion location (range) of a histologically proven colorectal polyp (adenoma) and is not displayed in the actual analysis result image. The colorectal polyp (adenoma) indicated by the rectangular frame 136 was captured from either side or a portion thereof was captured. Thus, the colorectal polyp is considered not to have been detected by the convolutional neural network.

FIG. 22D illustrates, as a false-negative image, an endoscopic image containing a colorectal polyp (adenoma) that was not detected, or missed, by the convolutional neural network. Rectangular frame 138 indicates, for reference, a lesion location (range) of a histologically proven colorectal polyp (adenoma) and is not displayed in the actual analysis result image. The colorectal polyp (adenoma) indicated by the rectangular frame 138 was very large and was less likely to be recognized. Thus, the colorectal polyp is considered not to have been detected by the convolutional neural network.

FIG. 22E illustrates, as false-positive images, an endoscopic image and an analysis result image containing an ileocecal valve (normal structure) that was incorrectly detected and classified by the convolutional neural network. As illustrated in FIG. 22E, the analysis result image shows rectangular frame 140 indicating a lesion location (range) estimated by the convolutional neural network, a lesion name (Others: The others), and a probability score (0.62).

FIG. 22F illustrates, as false-positive images, an endoscopic image and an analysis result image containing a normal colonic fold that was incorrectly detected and classified by the convolutional neural network. As illustrated in FIG. 22F, the analysis result image shows rectangular frame 142 indicating a lesion location (range) estimated by the convolutional neural network, a lesion name (adenoma: Adenoma), and a probability score (0.32).

FIG. 22G illustrates, as false-positive images, an endoscopic image and an analysis result image containing halation (artificial anomaly image) that was incorrectly detected and classified by the convolutional neural network. As illustrated in FIG. 22G, the analysis result image shows rectangular frame 144 indicating a lesion location (range) estimated by the convolutional neural network, a lesion name (adenoma: Adenoma), and a probability score (0.43).

FIG. 22H illustrates, as false-positive images, an endoscopic image and an analysis result image containing a polyp that was incorrectly detected and classified by the convolutional neural network. The polyp was suspected to be a true polyp, but not finally confirmed. As illustrated in FIG. 22H, the analysis result image shows rectangular frame 146 indicating a lesion location (range) estimated by the convolutional neural network, a lesion name (hyperplastic polyp: Hyperplastic), and a probability score (0.48).

Next, a third assessment test for determining advantageous effects achieved with the configuration of the embodiment described above will be described.

[Preparation of Learning Data Sets]

Endoscopic image of the esophagus, the number of which was 8,428 (384 patients), which were obtained from February 2016 to April 2017, were prepared as learning data sets (teacher data) to be used for learning a convolutional neural network in a diagnostic imaging support apparatus. The endoscopic images contain esophageal cancer histologically proven by a certified pathologist (specifically, squamous cell carcinoma (ESCC) or adenocarcinoma (EAC)). Endoscopy was performed for screening in daily clinical practice or preoperative examination, and the endoscopic images were collected using standard endoscopes (GIF-H290Z, GIF-H290, GIF-XP290N, GIF-H260Z, GIF-H260, Olympus Medical Systems Corp., Tokyo) and standard endoscopic video systems (EVIS LUCERA CV-260/CLU-260, EVIS LUCERA ELITE CV-290/CLV-290SL, Olympus Medical Systems Corp.).

The endoscopic images serving as learning data sets included endoscopic images captured with white light illumination on the esophagus of the subject, and endoscopic images captured with narrow-band light (NBI narrow-band light) illumination on the esophagus of the subject. Endoscopic images with poor image quality due to halation, fogging of lens, defocusing, mucus, insufficient air supply, or the like were excluded from the learning data sets.

Finally, 8,428 endoscopic images for histologically proven esophageal cancers were collected as learning data sets. The endoscopic images contained 397 lesions of squamous cell carcinoma, which were 332 lesions of superficial esophageal cancer and 65 lesions of advanced gastric cancer, and 32 lesions of adenocarcinoma, which were 19 lesions of superficial esophageal cancer and 13 lesions of advanced gastric cancer. An experienced endoscopist with 2,000 or more cases of upper endoscopy performed the precise manual setting of marking for feature extraction on lesion names (superficial esophageal cancer or advanced esophageal cancer) and lesion locations of all esophageal cancers (squamous cell carcinoma or adenocarcinoma) in the collected endoscopic images.

[Learning/Algorithm]

To construct a diagnostic imaging support apparatus, a convolutional neural network based on a Single Shot MultiBox Detector (SSD, https://arxiv.org/abs/1512.02325) and constituted by 16 or more layers was used. The Caffe deep learning framework, which was developed in Berkeley Vision and Learning Center (BVLC), was used for learning and an assessment test. All the layers of the convolutional neural network are finely adjusted with a global learning rate of 0.0001 by using the stochastic gradient descent method. To ensure compatibility with CNN, each image was resized to 300×300 pixels. In accordance with the resizing of each image, the marking size was changed for the lesion location of the lesion.

[Preparation of Assessment Test Data Sets]

To assess the diagnostic accuracy of the constructed convolutional-neural-network-based diagnostic imaging support apparatus, 1,118 endoscopic images (esophagus) for 97 patients (47 patients: having 49 lesions of esophageal cancer, 50 patients: having no esophageal cancer) who underwent endoscopy as a normal clinical examination were collected as assessment test data sets. As a result, of the 47 patients, 45 patients had 1 lesion of esophageal cancer, and 2 patients had 2 lesions of esophageal cancer. The endoscopic images used as assessment test data sets included, like the learning data sets, endoscopic images captured with white light illumination on the esophagus of the subject, and endoscopic images captured with narrow-band light (NBI narrow-band light) illumination on the esophagus of the subject.

FIG. 23 is a diagram illustrating features of patients (n=47) and lesions (n=49) related to endoscopic images used for assessment test data sets. As illustrated in FIG. 23, the median of the tumor sizes (diameters) was 20 mm, and the range of the tumor sizes (diameters) was 5 to 700 mm. In macroscopic classification, there were 43 lesions of the superficial type (type 0-I, type 0-IIa, type 0-IIb, and type 0-IIc), the number of which was larger than that of the advanced type (6 lesions). In terms of tumor depth, there were 42 lesions of superficial esophageal cancer (mucosal cancer: T1a, submucosal cancer: T1b), and 7 lesions of advanced gastric cancer (T2-T4). In histopathology, there were 41 lesions of squamous cell carcinoma, and 8 lesions of adenocarcinoma.

[Method for Assessment Test]

In this assessment test, assessment test data sets were input to a diagnostic imaging support apparatus based on a convolutional neural network on which a learning process was performed using learning data sets, and it was assessed whether esophageal cancer was correctly detected from each of the endoscopic images constituting the assessment test data sets. A correct detection of esophageal cancer was regarded as a "correct answer". Upon detection of an esophageal cancer from the endoscopic images, the convolutional neural network outputs the lesion name (superficial esophageal cancer or advanced esophageal cancer), the lesion location, and the probability score.

To acquire results of the assessment test, the assessment test was conducted using the following definitions.

(Definition 1)

In this assessment test, if the convolutional neural network detected at least a part of esophageal cancer, it was determined that the convolutional neural network detected esophageal cancer, and this case was regarded as a correct answer. This is because it may be difficult to recognize the entire edge of esophageal cancer in some endoscopic images. Note that in this assessment test, even when esophageal cancer is actually present within a rectangular frame indicating a lesion location (range) of esophageal cancer detected by the convolutional neural network, it was determined that the convolutional neural network failed to detect esophageal cancer if the rectangular frame includes a non-esophageal cancer site in a wide range (80% or more of the endoscopic image).

(Definition 2)

In this assessment test, only when in endoscopic images related to 2 patients having 2 lesions of esophageal cancer, the convolutional neural network detected the 2 lesions, it was determined that the convolutional neural network detected esophageal cancer, and this case was regarded as a correct answer.

(Definition 3)

In this assessment test, if the convolutional neural network detected at least one non-esophageal cancer site as esophageal cancer in an endoscopic image containing no esophageal cancer, it was determined that the convolutional neural network erroneously detected esophageal cancer, and the site was regarded as a false-positive. Note that in this assessment test, when the convolutional neural network erroneously detected two non-esophageal cancer sites as esophageal cancer in a single endoscopic image containing no esophageal cancer, the sites were counted as a single false-positive, rather than two.

In this assessment test, furthermore, the sensitivity, specificity, positive predictive value (PPV), and negative predictive value (NPV) for the diagnostic capability of the convolutional neural network to detect esophageal cancer in each endoscopic image were calculated using following equations 1 to 4.

Sensitivity=(the number of endoscopic images in which the convolutional neural network correctly detected esophageal cancer)/(the number of endoscopic images included in the assessment test data sets and containing esophageal cancer)  (Equation 1)

Specificity=(the number of endoscopic images in which the convolutional neural network correctly detected non-presence of esophageal cancer)/(the number of endoscopic images included in the assessment test data sets and containing no esophageal cancer)  (Equation 2)

Positive predictive value=(the number of endoscopic images in which the convolutional neural network correctly detected esophageal cancer)/(the number of endoscopic images in which the convolutional neural network detected esophageal cancer)  (Equation 3)

Negative predictive value=(the number of endoscopic images in which the convolutional neural network correctly detected non-presence of esophageal cancer)/(the number of endoscopic images in which the convolutional neural network detected non-presence of esophageal cancer) (Equation 4)

[Results of Assessment Test]

The convolutional neural network finished a process for analyzing 1,118 endoscopic images constituting assessment test data sets in 27 seconds. Notably, the convolutional neural network correctly detected all (seven) esophageal cancers whose tumor sizes were less than 10 mm The positive predictive value for the diagnostic capability of the convolutional neural network was 40%, with shadow and normal structures being misdiagnosed, whereas the negative predictive value was 95%. In addition, the convolutional neural network correctly detected the classification of esophageal cancers (superficial esophageal cancer or advanced esophageal cancer) with an accuracy of 98%.

Figure 24A:
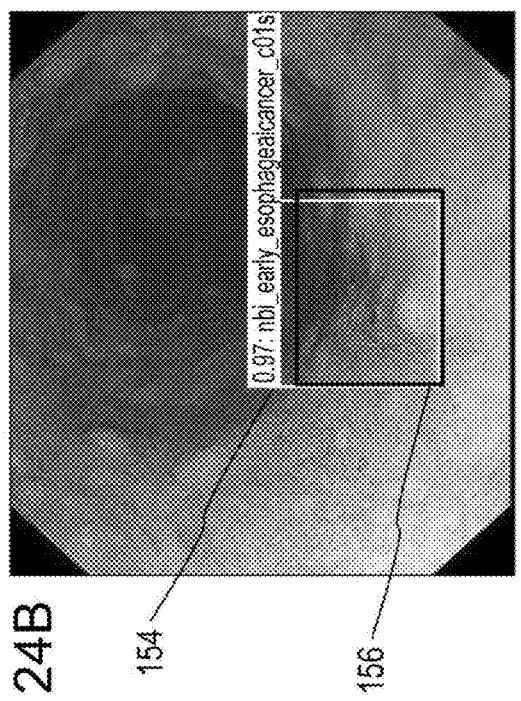
FIGS. 24A, 24B, 24C, and 24D are diagrams illustrating an example of endoscopic images and analysis result images in a third assessment test.

FIGS. 24A, 24B, 24C, and 24D are diagrams illustrating an example of endoscopic images and analysis result images in the third assessment test. FIG. 24A illustrates an endoscopic image (an endoscopic image captured with white light illumination on the esophagus of the subject) and an analysis result image containing esophageal cancer that was correctly detected and classified by the convolutional neural network. As illustrated in FIG. 24A, the analysis result image shows rectangular frame 150 indicating a lesion location (range) estimated by the convolutional neural network, a lesion name (superficial esophageal cancer), and a probability score (0.91). Rectangular frame 152 indicates, for reference, a lesion location (range) of a histologically proven esophageal cancer and is not displayed in the actual analysis result image.

Figure 24B:
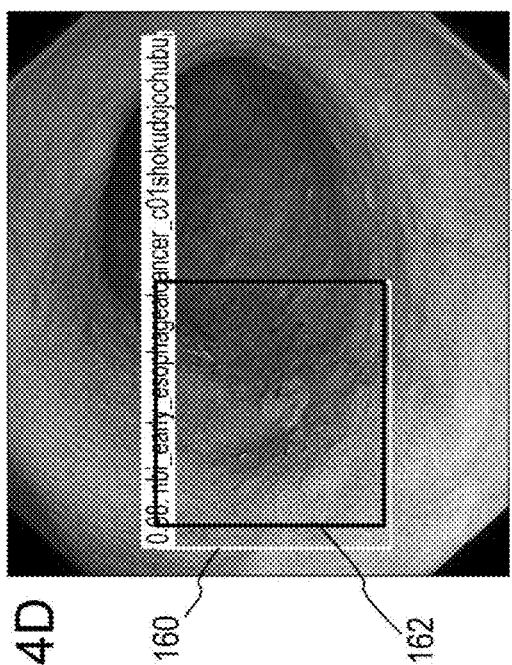

FIG. 24B corresponds to FIG. 24A and illustrates an endoscopic image (an endoscopic image captured with NBI narrow-band light illumination on the esophagus of the subject) and an analysis result image containing esophageal cancer that was correctly detected and classified by the convolutional neural network. As illustrated in FIG. 24B, the analysis result image shows rectangular frame 154 indicating a lesion location (range) estimated by the convolutional neural network, a lesion name (superficial esophageal cancer), and a probability score (0.97). Rectangular frame 156 indicates, for reference, a lesion location (range) of a histologically proven esophageal cancer and is not displayed in the actual analysis result image.

Figure 24C:
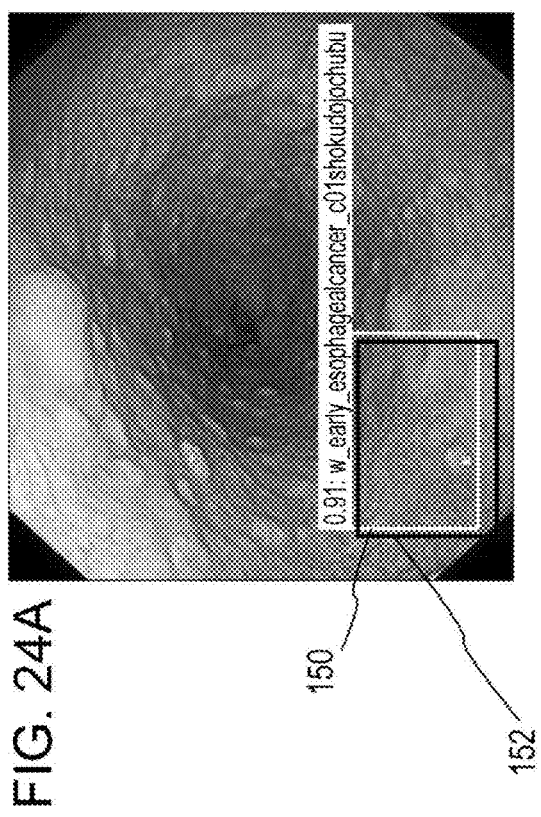

FIG. 24C illustrates, as a false-negative image, an endoscopic image (an endoscopic image captured with white light illumination on the esophagus of the subject) containing esophageal cancer that was not detected, or missed, by the convolutional neural network. Rectangular frame 158 indicates, for reference, a lesion location (range) of a histologically proven esophageal cancer and is not displayed in the actual analysis result image.

Figure 24D:
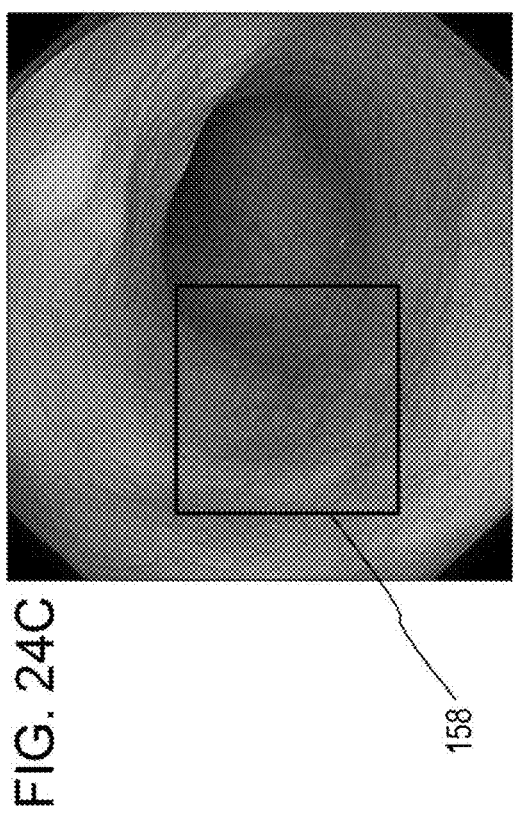

FIG. 24D corresponds to FIG. 24C and illustrates an endoscopic image (an endoscopic image captured with NBI narrow-band light illumination on the esophagus of the subject) and an analysis result image containing esophageal cancer that was correctly detected and classified by the convolutional neural network. As illustrated in FIG. 24D, the analysis result image shows rectangular frame 160 indicating a lesion location (range) estimated by the convolutional neural network, a lesion name (superficial esophageal cancer), and a probability score (0.98). Rectangular frame 162 indicates, for reference, a lesion location (range) of a histologically proven esophageal cancer and is not displayed in the actual analysis result image.

Figure 26:
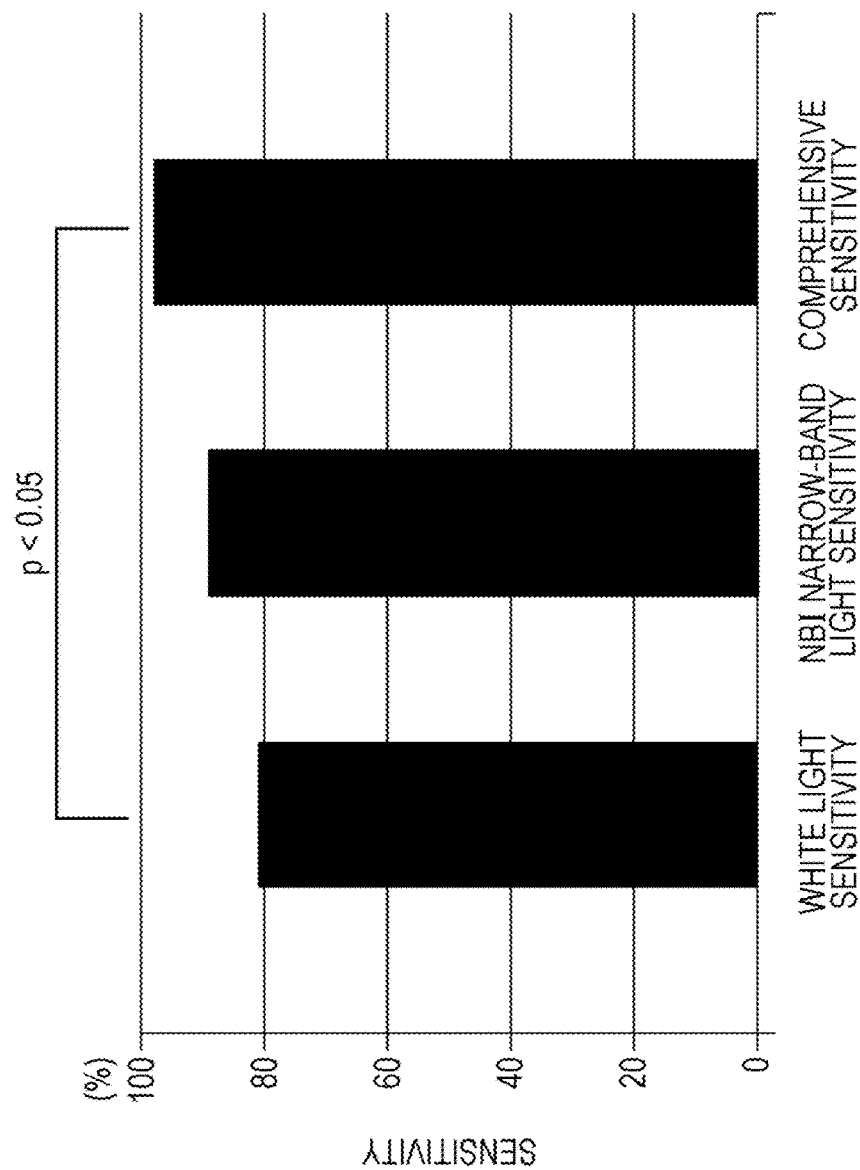
FIG. 26 is a diagram illustrating white light sensitivity, NBI narrow-band light sensitivity, and comprehensive sensitivity.

FIG. 25 is a diagram illustrating detection results of esophageal cancer/non-esophageal cancer by the convolutional neural network and detection results of esophageal cancer/non-esophageal cancer via biopsy for the cases (esophageal cancer) of 47 patients having esophageal cancer and the cases (non-esophageal cancer) of 50 patients having no esophageal cancer. In FIG. 25, in this assessment test, when the convolutional neural network correctly detected esophageal cancer/non-esophageal cancer in an endoscopic image captured with at least one of white light and NBI narrow-band light illumination on the esophagus of the subject in comprehensive diagnostic results, it was determined that the convolutional neural network correctly detected esophageal cancer/non-esophageal cancer. As illustrated in FIG. 25, in comprehensive diagnosis, the convolutional neural network correctly detected esophageal cancer in 98% (46/47) of cases of esophageal cancer present in endoscopic images. Further, although not illustrated, the convolutional neural network correctly detected all esophageal cancers whose tumor sizes were less than 10 mm FIG. 26 is a diagram illustrating, in the cases illustrated in FIG. 25, sensitivity for the endoscopic images captured with illumination of white light (hereinafter referred to as white light sensitivity), sensitivity for the endoscopic images captured with illumination of NBI narrow-band light (hereinafter referred to as NBI narrow-band light sensitivity), and sensitivity for the endoscopic images captured with illumination of at least one of white light and NBI narrow-band light (hereinafter referred to as comprehensive sensitivity). As illustrated in FIG. 26, in the cases illustrated in FIG. 25, NBI narrow-band light sensitivity (89%) was higher than white light sensitivity (81%), and comprehensive sensitivity (98%) was much higher than white light sensitivity. The white light sensitivity, NBI narrow-band light sensitivity, and comprehensive sensitivity for squamous cell carcinoma were 79%, 89%, and 97%, respectively. The white light sensitivity, NBI narrow-band light sensitivity, and comprehensive sensitivity for adenocarcinoma were 88%, 88%, and 100%, respectively.

Figure 28:
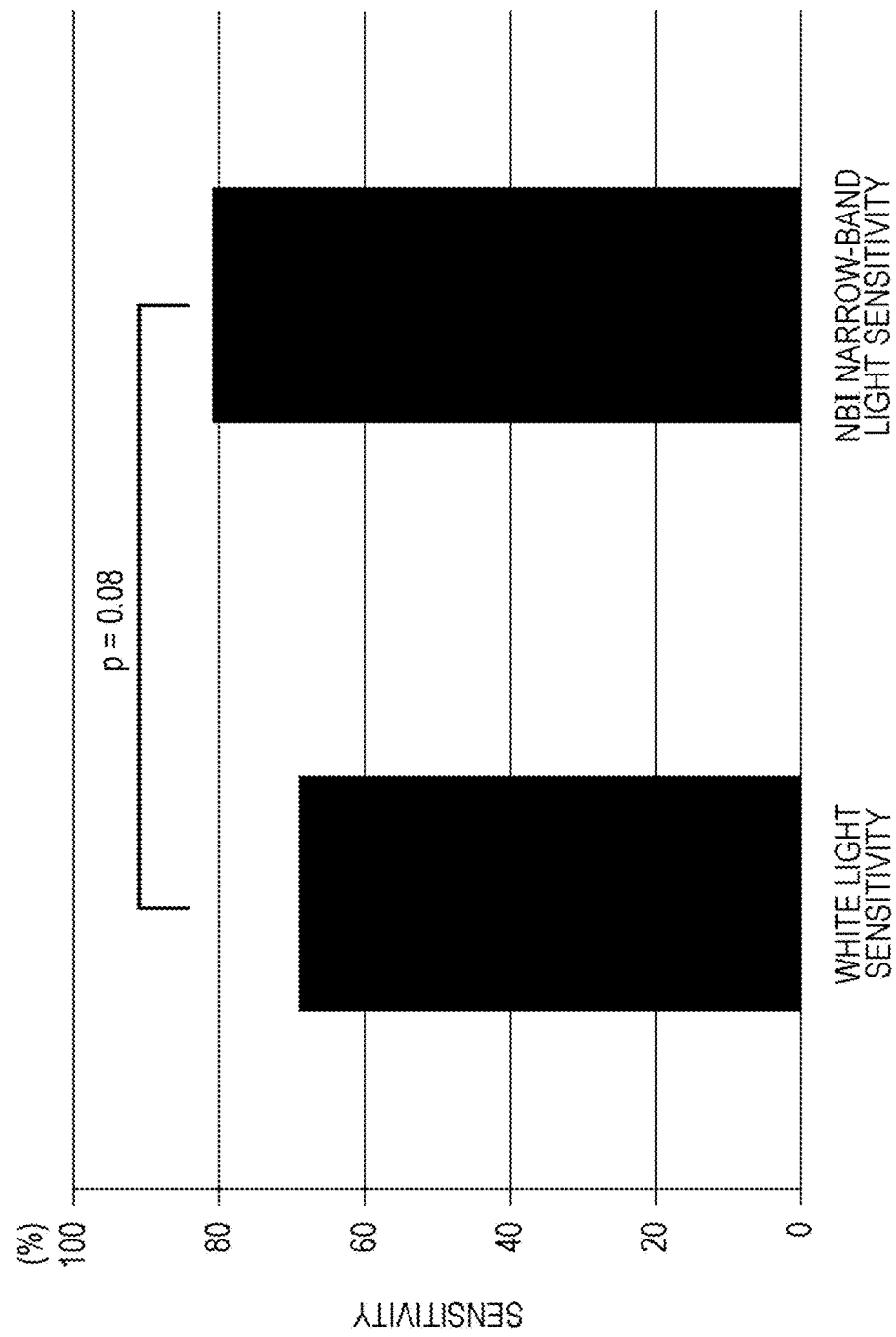
FIG. 28 is a diagram illustrating white light sensitivity and NBI narrow-band light sensitivity.

FIG. 27 is a diagram illustrating detection results of esophageal cancer/non-esophageal cancer by the convolutional neural network and detection results of esophageal cancer/non-esophageal cancer via biopsy for endoscopic images captured with illumination of white light or NBI narrow-band light. FIG. 28 is a diagram illustrating, in the endoscopic images illustrated in FIG. 27, sensitivity for the endoscopic images captured with illumination of white light (hereinafter referred to as white light sensitivity), and sensitivity for the endoscopic images captured with illumination of NBI narrow-band light (hereinafter referred to as NBI narrow-band light sensitivity).

As illustrated in FIG. 27, the convolutional neural network correctly detected esophageal cancer in 74% (125/168) of endoscopic images for which the presence of esophageal cancer was diagnosed as bioptic results. The sensitivity, specificity, positive predictive value, and negative predictive value for the diagnostic capability of the convolutional neural network were 74%, 80%, 40%, and 95%, respectively. As illustrated in FIG. 28, NBI narrow-band light sensitivity (81%) was higher than white light sensitivity (69%). The white light sensitivity and NBI narrow-band light sensitivity for squamous cell carcinoma were 72% and 84%, respectively. The white light sensitivity and NBI narrow-band light sensitivity for adenocarcinoma were 55% and 67%, respectively.

The present inventors have reviewed the degree of match between the classification of esophageal cancer detected and classified by the convolutional neural network (CNN classification) and the classification of a histologically proven esophageal cancer (depth of invasion) as the classification accuracy of the convolutional neural network. FIG. 29 is a diagram illustrating degrees of match between CNN classification and the depth of invasion.

As illustrated in FIG. 29, in endoscopic images captured with white light illumination on the esophagus of the subject, the classification of esophageal cancers that accounted for 100% (89/89) of the total was correctly performed by the convolutional neural network. That is, esophageal cancers that account 100% (75/75) of the esophageal cancers histologically proven as superficial esophageal cancer were correctly classified as superficial esophageal cancer by the convolutional neural network. Esophageal cancers that accounted for 100% (14/14) of the esophageal cancers histologically proven as advanced esophageal cancer were correctly classified as advanced esophageal cancer by the convolutional neural network.

In endoscopic images captured with NBI narrow-band light illumination on the esophagus of the subject, the classification of esophageal cancers that accounted for 96% (76/79) of the total was correctly performed by the convolutional neural network.

Esophageal cancers that accounted for 99% (67/68) of the esophageal cancers histologically proven as superficial esophageal cancer were correctly classified as superficial esophageal cancer by the convolutional neural network. Further, esophageal cancers that accounted for 82% (9/11) of the esophageal cancers histologically proven as advanced esophageal cancer were correctly classified as advanced esophageal cancer by the convolutional neural network.

In endoscopic images captured with white light or NBI narrow-band light illumination on the esophagus of the subject, the classification of esophageal cancers that accounted for 98% (165/168) of the total were correctly classified by the convolutional neural network. Esophageal cancers that accounted for 99% (142/143) of the esophageal cancers histologically proven as superficial esophageal cancer were correctly classified as superficial esophageal cancer by the convolutional neural network. Further, esophageal cancers that accounted for 92% (23/25) of the esophageal cancers histologically proven as advanced esophageal cancer were correctly classified as advanced esophageal cancer by the convolutional neural network. In the manner described above, the classification accuracy of the convolutional neural network was found to be very high. The classification accuracies of the convolutional neural network for squamous cell carcinoma and adenocarcinoma were 99% (146/147) and 90% (19/21), respectively.

To improve the diagnostic capability of the convolutional neural network, it is important to identify the reason that the convolutional neural network incorrectly detected esophageal cancer and the reason that the convolutional neural network failed to correctly detect the true esophageal cancer, that is, the convolutional neural network missed the true esophageal cancer. Accordingly, the present inventors have reviewed all of the endoscopic images (false-positive images) in which esophageal cancers were incorrectly detected by the convolutional neural network and all of the endoscopic images (false-negative images) in which true esophageal cancers were not detected by the convolutional neural network, and classified the images into several categories.

FIG. 30 is a diagram illustrating classification results of false-positive images and false-negative images. As illustrated in FIG. 30, among 188 false-positive images, 95 false-positive images (50%) contained shadow. Further, 61 false-positive images (32%) contained normal structures easily identified as esophageal cancer, the majority of which were the esophageal gastric junction (EGJ) or the left main bronchus. Further, 32 false-positive images (17%) contained benign lesions likely to be misdiagnosed as esophageal cancer, the majority of which were a postoperative scar, focal atrophy, Barrett's esophagus, and inflammation.

Figure 31C:
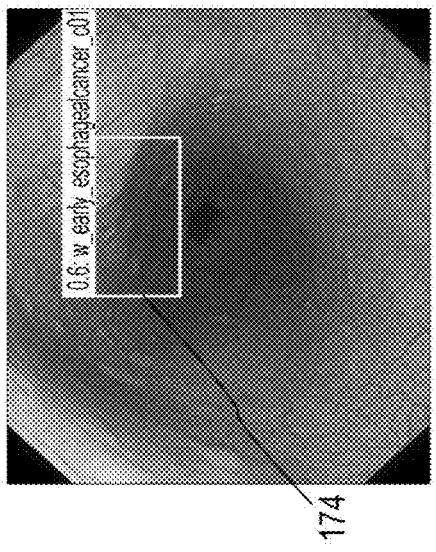
FIGS. 31A, 31B, 31C, 31D, 31E, and 31F are diagrams illustrating, as false-positive images, endoscopic images and analysis result images for incorrect detection and classification using the convolutional neural network.
Figure 31B:
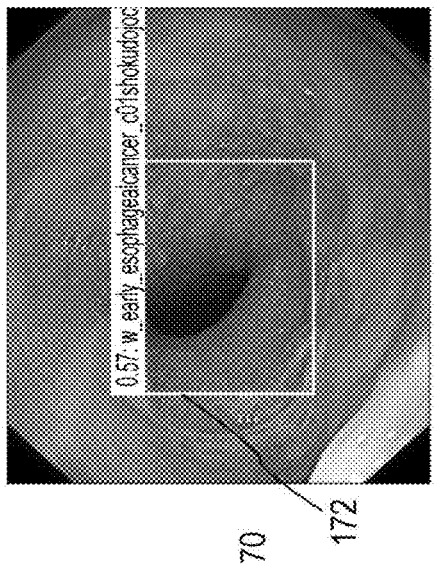
Figure 31A:
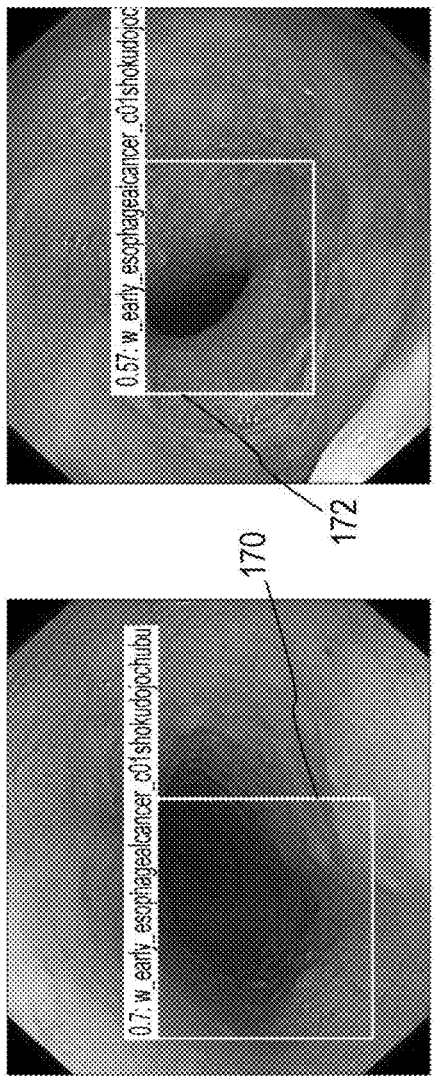

FIG. 31A is a diagram illustrating, as false-positive images, an endoscopic image and an analysis result image containing shadow, which was incorrectly detected and classified by the convolutional neural network. As illustrated in FIG. 31A, the analysis result image shows rectangular frame 170 indicating a lesion location (range) estimated by the convolutional neural network, a lesion name (superficial esophageal cancer), and a probability score (0.70).

FIG. 31B is a diagram illustrating, as false-positive images, an endoscopic image and an analysis result image containing a normal structure (the esophageal gastric junction) easily identified as esophageal cancer, which was incorrectly detected and classified by the convolutional neural network. As illustrated in FIG. 31B, the analysis result image shows rectangular frame 172 indicating a lesion location (range) estimated by the convolutional neural network, a lesion name (superficial esophageal cancer), and a probability score (0.57).

FIG. 31C is a diagram illustrating, as false-positive images, an endoscopic image and an analysis result image containing a normal structure (the left main bronchus) easily identified as esophageal cancer, which was incorrectly detected and classified by the convolutional neural network. As illustrated in FIG. 31C, the analysis result image shows rectangular frame 174 indicating a lesion location (range) estimated by the convolutional neural network, a lesion name (superficial esophageal cancer), and a probability score (0.60).

Figure 31F:
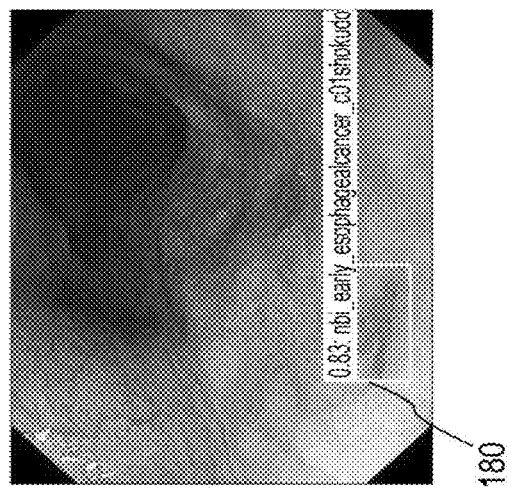
Figure 31E:
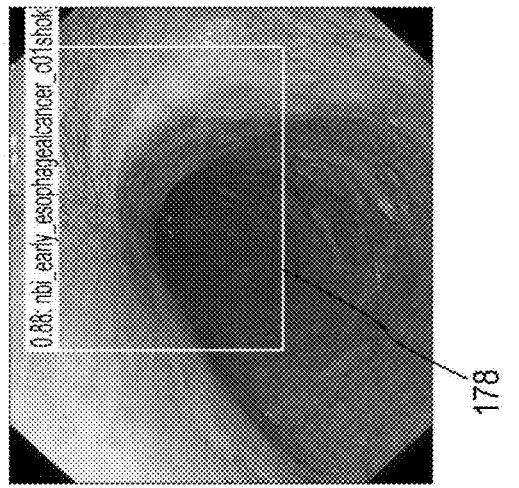
Figure 31D:
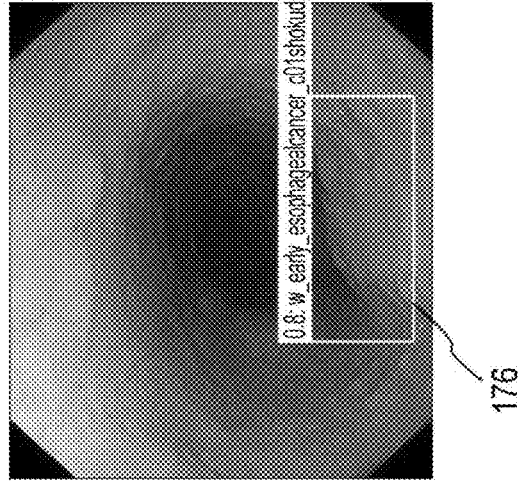

FIG. 31D is a diagram illustrating, as false-positive images, an endoscopic image and an analysis result image containing a normal structure (the vertebral body) easily identified as esophageal cancer, which was incorrectly detected and classified by the convolutional neural network. As illustrated in FIG. 31D, the analysis result image shows rectangular frame 176 indicating a lesion location (range) estimated by the convolutional neural network, a lesion name (superficial esophageal cancer), and a probability score (0.80).

FIG. 31E is a diagram illustrating, as false-positive images, an endoscopic image and an analysis result image containing a benign lesion (postoperative scar) likely to be misdiagnosed as esophageal cancer, which was incorrectly detected and classified by the convolutional neural network. As illustrated in FIG. 31E, the analysis result image shows rectangular frame 178 indicating a lesion location (range) estimated by the convolutional neural network, a lesion name (superficial esophageal cancer), and a probability score (0.88).

FIG. 31F is a diagram illustrating, as false-positive images, an endoscopic image and an analysis result image containing a benign lesion (focal atrophy) likely to be misdiagnosed as esophageal cancer, which was incorrectly detected and classified by the convolutional neural network. As illustrated in FIG. 31F, the analysis result image shows rectangular frame 180 indicating a lesion location (range) estimated by the convolutional neural network, a lesion name (superficial esophageal cancer), and a probability score (0.83).

As illustrated in FIG. 30, furthermore, in 10 false-negative images (25%) among 41 false-negative images, as a result of being misdiagnosed as inflammation of background mucosa by the convolutional neural network, the lesion is considered not to have been detected as a true esophageal cancer. Further, in 7 false-negative images (17%), due to a blurred image of squamous cell carcinoma irradiated with NBI narrow-band light, the squamous cell carcinoma is considered not to have been detected as a true esophageal cancer by the convolutional neural network.

Further, in 4 false-negative images (10%), Barrett's esophageal adenocarcinoma was present, but is considered not to have been detected as a true esophageal cancer due to insufficient learning about adenocarcinoma. Further, in 20 false-negative images (49%), the lesions are considered not to have been detected as true esophageal cancers by the convolutional neural network since the lesions were difficult to diagnose, such as a lesion appearing in the background of an endoscopic image or only a portion of a lesion present in an endoscopic image.

Figure 32C:
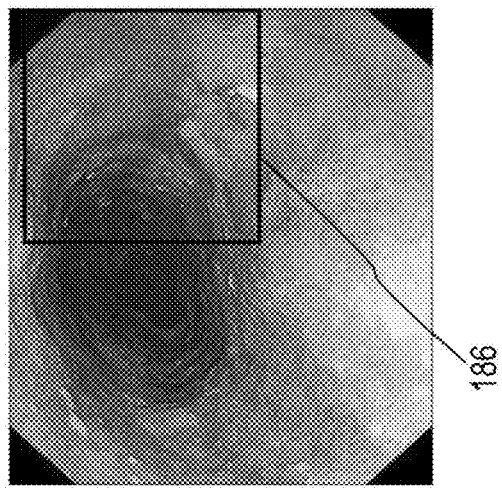
FIGS. 32A, 32B, 32C, 32D, and 32E are diagrams illustrating, as false-negative images, endoscopic images containing esophageal cancer that was not detected by the convolutional neural network.
Figure 32B:
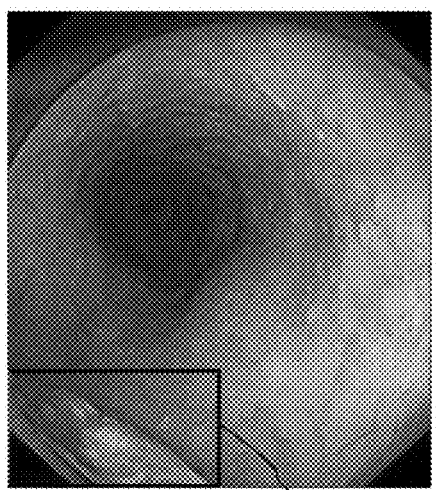
Figure 32E:
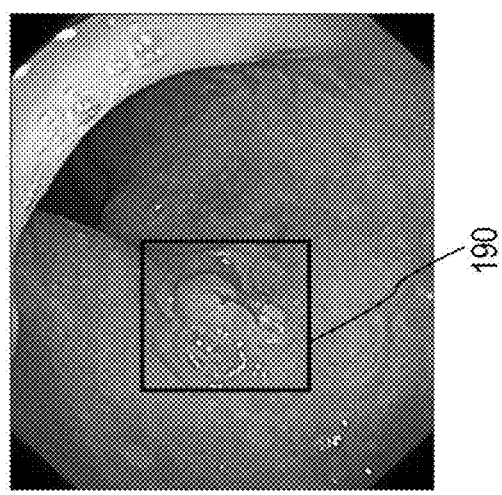
Figure 32A:
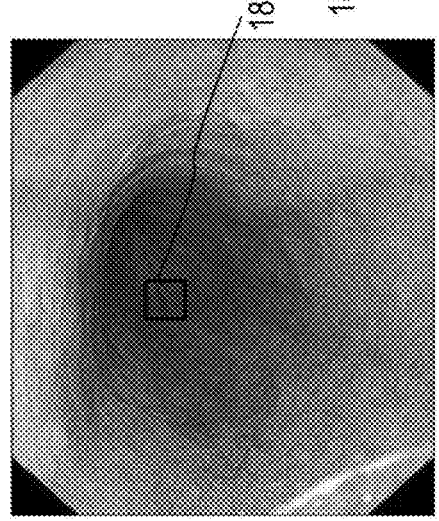

FIG. 32A is a diagram illustrating, as a false-negative image, an endoscopic image containing an esophageal cancer that was not detected by the convolutional neural network since the lesion appeared in the background of the endoscopic image and was difficult to diagnose. Rectangular frame 182 indicates, for reference, a lesion location (range) of a histologically proven esophageal cancer and is not displayed in the actual analysis result image.

FIG. 32B is a diagram illustrating, as a false-negative image, an endoscopic image containing an esophageal cancer that was not detected by the convolutional neural network since the lesion, only a portion of which was present in the endoscopic image, was difficult to diagnose. Rectangular frame 184 indicates, for reference, a lesion location (range) of a histologically proven esophageal cancer and is not displayed in the actual analysis result image.

FIG. 32C is a diagram illustrating, as a false-negative image, an endoscopic image containing an esophageal cancer that was not detected by the convolutional neural network as a result of being misdiagnosed as inflammation of background mucosa. Rectangular frame 186 indicates, for reference, a lesion location (range) of a histologically proven esophageal cancer and is not displayed in the actual analysis result image.

Figure 32D:
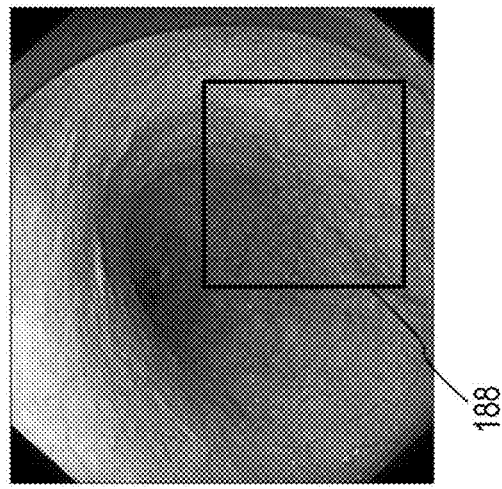

FIG. 32D is a diagram illustrating, as a false-negative image, an endoscopic image containing an esophageal cancer that was not detected by the convolutional neural network due to a blurred image of squamous cell carcinoma irradiated with NBI narrow-band light. Rectangular frame 188 indicates, for reference, a lesion location (range) of a histologically proven esophageal cancer and is not displayed in the actual analysis result image.

FIG. 32E is a diagram illustrating, as a false-negative image, an endoscopic image containing esophageal cancer (Barrett's esophageal adenocarcinoma) that was not detected by the convolutional neural network due to insufficient learning about adenocarcinoma although Barrett's esophageal adenocarcinoma was present. Rectangular frame 190 indicates, for reference, a lesion location (range) of a histologically proven esophageal cancer and is not displayed in the actual analysis result image.

As indicated from the results of the third assessment test described above, the convolutional neural network effectively detects esophageal cancer with considerable accuracy at a remarkable speed even if the esophageal cancer is small, and is likely to be useful to reduce failure of detection of esophageal cancer in endoscopy of the esophagus. It is also indicated that the convolutional neural network is able to correctly classify detected esophageal cancers and strongly support an endoscopist in diagnosis based on endoscopic images. It is considered that more learning processes are performed on the convolutional neural network to achieve higher diagnostic accuracy.

The disclosure of Japanese Patent Application No. 2017-209232 filed on Oct. 30, 2017, Japanese Patent Application No. 2018-007967 filed on Jan. 22, 2018, and Japanese Patent Application No. 2018-038828 filed on Mar. 5, 2018, including the specification, drawings and abstract, is incorporated herein by reference in its entirety.

INDUSTRIAL APPLICABILITY

The present invention is suitable for use in a diagnostic imaging support apparatus, a data collection method, a diagnostic imaging support method, and a diagnostic imaging support program that are capable of supporting an endoscopist in diagnosis with endoscopic images.

REFERENCE SIGNS LIST

10 Endoscopic image acquisition section
20 Lesion estimation section
30 Display control section
40 Learning apparatus
100 Diagnostic imaging support apparatus
101 CPU
102 ROM
103 RAM
104 External storage apparatus
105 Communication interface
200 Endoscopic image capturing apparatus
300 Display apparatus
D1 Endoscopic image data
D2 Estimation result data
D3 Analysis result image data
D4 Teacher data

What is claimed is:

1. A diagnostic imaging support apparatus, comprising:
at least one or more processors configured to:
obtain a digestive-organ endoscopic image of a subject captured by an endoscope or an endoscopic video system;
estimate a location of a lesion present in the digestive-organ endoscopic image of the subject and information on certainty of the location of the lesion using a convolutional neural network;
perform control to generate an analysis result image showing the location of the lesion and the certainty of the location of the lesion and to display the analysis result image on the digestive-organ endoscopic image,
wherein the convolutional neural network is subjected to a learning process based on lesion locations of lesions present in a plurality of digestive-organ tumor endoscopic images of a plurality of subjects, the lesion locations of the lesions being determined in advance through feature extraction of atrophy, intestinal metaplasia, mucosal swelling or depression, and a condition of mucosal color tones,
change a display style of lesion location information identifying the location of the lesion in the analysis result image in accordance with the certainty, wherein the information on the certainty of the location of the lesion is indicated as a probability score; and change a display color of lesion location information identifying the location of the lesion in the analysis result image when the probability score is higher than a predetermined score.

2. The diagnostic imaging support apparatus according to claim 1, wherein
the plurality of digestive-organ tumor endoscopic images include an endoscopic image captured with white light illumination on a digestive organ of the subject.

3. The diagnostic imaging support apparatus according to claim 1, wherein
the plurality of digestive-organ tumor endoscopic images include an endoscopic image captured with a dye applied to a digestive organ of the subject of the plurality of subjects.

4. The diagnostic imaging support apparatus according to claim 1, wherein
the plurality of digestive-organ tumor endoscopic images include an endoscopic image captured with narrow-band light illumination on a digestive organ of the subject of the plurality of subjects.

5. The diagnostic imaging support apparatus according to claim 1, wherein
the digestive organ includes a stomach.

6. The diagnostic imaging support apparatus according to claim 1, wherein the digestive organ includes an esophagus.

7. The diagnostic imaging support apparatus according to claim 1, wherein the digestive organ includes a duodenum.

8. The diagnostic imaging support apparatus according to claim 1, wherein the digestive organ includes a large intestine.

9. A data collection method for collecting, using the diagnostic imaging support apparatus according to claim 1, the analysis result image includes data related to a gastrointestinal tract lesion for a gastrointestinal tract of a subject.

10. The diagnostic imaging support apparatus according to claim 1, wherein the information on certainty of the location of the lesion is indicated as a probability score and the probability score is represented by a value greater than 0 and less than or equal to 1 or a value of 0% to 100%.

11. The diagnostic imaging support apparatus according to claim 1, wherein the convolutional neural network is subjected to a learning process further based on information related to age, gender, geographic area, or past medical history of each of the plurality of subjects.

12. The diagnostic imaging support apparatus according to claim 1, wherein the one or more processors is further configured to perform pre-processing prior to the estimation of the location of a lesion present in a digestive-organ endoscopic image, the pre-processing includes conversion into a size or an aspect ratio of the digestive-organ endoscopic image, color separation processing of the digestive-organ endoscopic image, color conversion processing of the digestive-organ endoscopic image, color extraction processing, or brightness gradient extraction processing.

13. A diagnostic imaging support method using an apparatus, the diagnostic imaging support method comprising:
obtaining a digestive-organ endoscopic image of a subject captured by an endoscope or an endoscopic video system;
estimating a location of a lesion present in the digestive-organ endoscopic image of the subject and information on certainty of the location of the lesion using a convolutional neural network,
performing control to generate an analysis result image showing the location of the lesion and the certainty of the location of the lesion and to display the analysis result image on the digestive-organ endoscopic image,
subjecting the convolutional neural network to a learning process based on lesion locations of lesions present in a plurality of digestive-organ tumor endoscopic images of a plurality of subjects, the lesion locations of the lesions being determined in advance through feature extraction of atrophy, intestinal metaplasia, mucosal swelling or depression, and a condition of mucosal color tones,
changing a display style of lesion location information identifying the location of the lesion in the analysis result image in accordance with the certainty, wherein the information on the certainty of the location of the lesion is indicated as a probability score, and
changing a display color of lesion location information identifying the location of the lesion in the analysis result image when the probability score is higher than a predetermined score.

14. A non-transitory computer-readable storage medium storing a diagnostic imaging support program for causing a computer to execute:
a process of obtaining a digestive-organ endoscopic image of a subject captured by an endoscope or an endoscopic video system;
a process of estimating a location of a lesion present in the digestive-organ endoscopic image of the subject and information on certainty of the location of the lesion using a convolutional neural network,; and
a process of performing control to generate an analysis result image showing the location of the lesion and the certainty of the location of the lesion and to display the analysis result image on the endoscopic image, wherein the convolutional neural network is subjected to a learning process based on lesion locations of lesions present in a plurality of digestive-organ tumor endoscopic images of a plurality of subjects, the lesion locations of the lesions being determined in advance through feature extraction of atrophy, intestinal metaplasia, mucosal swelling or depression, and a condition of mucosal color tones,
a process of changing a display style of lesion location information identifying the location of the lesion in the analysis result image in accordance with the certainty, wherein the information on the certainty of the location of the lesion is indicated as a probability score, and
a process of changing a display color of lesion location information identifying the location of the lesion in the analysis result image when the probability score is higher than a predetermined score.

* * * * *